(12) United States Patent
Le Bonniec et al.

(10) Patent No.: US 7,589,178 B2
(45) Date of Patent: Sep. 15, 2009

(54) THROMBIN-CLEAVABLE CHIMERIC PROTEINS

(75) Inventors: Bernard Le Bonniec, Paris (FR); Pierre-Emmanuel Marque, Paris (FR); Virginie Louvain, Verrieres-le-Buisson (FR); Claire Calmel, Paris (FR); Elsa Bianchini, Paris (FR); Martine Aiach, Sevres (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 494 days.

(21) Appl. No.: 10/492,191

(22) PCT Filed: Oct. 18, 2002

(86) PCT No.: PCT/EP02/12191

§ 371 (c)(1),
(2), (4) Date: Mar. 11, 2005

(87) PCT Pub. No.: WO03/035861

PCT Pub. Date: May 1, 2003

(65) Prior Publication Data

US 2005/0202527 A1    Sep. 15, 2005

(30) Foreign Application Priority Data

Oct. 19, 2001  (FR) .................................. 01 13492

(51) Int. Cl.
*C07K 14/00* (2006.01)
*C07H 21/04* (2006.01)
*C12N 15/09* (2006.01)
(52) U.S. Cl. ........................... 530/384; 530/350; 514/2; 514/12; 536/23.1; 435/69.1; 435/325
(58) Field of Classification Search ............ 514/2, 514/12; 530/350, 384; 435/214, 325, 69.1; 536/23.1
See application file for complete search history.

(56) References Cited

U.S. PATENT DOCUMENTS

| 5,196,404 | A  |   | 3/1993  | Maraganore et al. |
|-----------|----|---|---------|-------------------|
| 5,589,571 | A  | * | 12/1996 | King .......................... 530/381 |
| 5,637,492 | A  | * | 6/1997  | Dawson et al. .............. 435/217 |
| 5,851,983 | A  |   | 12/1998 | Sugiyama et al. |
| 6,232,456 | B1 | * | 5/2001  | Cohen et al. ................ 536/23.1 |
| 6,573,071 | B1 |   | 6/2003  | Himmelspach et al. |
| 2006/0148038 | A1 |   | 7/2006  | Louvain et al. |

FOREIGN PATENT DOCUMENTS

EP    0319312    6/1989

OTHER PUBLICATIONS

Sefferenick et al., J. Bacteriology, vol. 183, pp. 2405-2410, 2001.*
Juengst E., "What next for human gene therapy?" BMJ, vol. 326, Jun. 2003, pp. 1410-1411.*
Perera et al: "Modeling Zymogen Protein C" Biophysical Journal, vol. 79, Dec. 2000, pp. 2925-2943, XP002205252, * See p. 2926 (Figures 1-2) and pp. 2934-2935 ("Activation peptide").
Richardson et al, Protein Science, (1994), vol. 3, pp. 711-712.
Hartmut J. Ehrlich, et al., "Direct Expression of Recombinant Activated Human Protein C, a Serine Protease", The Journal of Biological Chemistry, vol. 264, No. 24, 1989, 8 pages, p. 14298-14304.
Michele Himmelspach, et al., "Recombinant Human Factor X: High yield Expression and the Role of Furin in Proteolytic Maturation in Vivo and in Vitro", vol. 97, 2000, 18 pages, p. 51-67, Thrombosis Research.
Keith M. Dawson, et al., "Plasminogen Mutants Activated by Thrombin", The Journal of Biological Chemistry, vol. 269, No. 23, 1994, 5 pages, p. 15989-15992.

* cited by examiner

*Primary Examiner*—Chih-Min Kam
(74) *Attorney, Agent, or Firm*—Oblon, Spivak, McClelland, Maier & Neustadt, P.C.

(57) ABSTRACT

The invention relates to chimeric proteins comprising an artificial sequence for cleavage by thrombin, in which the activation peptide is fibrinopeptide A. Preferably, said chimeric proteins are derived from the zymogen of a serine protease such as PC or FX, by replacing the activation peptide of said zymogen with fibrinopeptide A, or a portion thereof, comprising at least amino acids $P_{10}$ to $P_1$ of said fibrinopeptide.

24 Claims, 7 Drawing Sheets

```
Ala Asn Ser Phe Leu Glu Glu Leu Arg His Ser Ser Leu Glu Arg Glu
1             5                 10                  15
Cys Ile Glu Glu Ile Cys Asp Phe Glu Glu Ala Lys Glu Ile Phe Gln
            20              25              30
Asn Val Asp Asp Thr Leu Ala Phe Trp Ser Lys His Val Asp Gly Asp
        35              40              45
Gln Cys Leu Val Leu Pro Leu Glu His Pro Cys Ala Ser Leu Cys Cys
    50              55              60
Gly His Gly Thr Cys Ile Asp Gly Ile Gly Ser Phe Ser Cys Asp Cys
65              70              75              80
Arg Ser Gly Trp Glu Gly Arg Phe Cys Gln Arg Glu Val Ser Phe Leu
            85              90              95
Asn Cys Ser Leu Asp Asn Gly Gly Cys Thr His Tyr Cys Leu Glu Glu
            100             105             110
Val Gly Trp Arg Arg Cys Ser Cys Ala Pro Gly Tyr Lys Leu Gly Asp
        115             120             125
Asp Leu Leu Gln Cys His Pro Ala Val Lys Phe Pro Cys Gly Arg Pro
    130             135             140
Trp Lys Arg Met Glu Lys Lys Arg Ser His Leu Lys Arg Asp Thr Glu
145             150             155             160
Asp Gln Glu Asp Gln Val Asp Pro Arg Leu Ile Asp Gly Lys Met Thr
            165             170             175
                                16                      21
ARG ARG GLY ASP SER PRO TRP GLN VAL VAL LEU LEU ASP SER LYS LYS
            180             185             190
            26              31              36
LYS LEU ALA CYS GLY ALA VAL LEU ILE HIS PRO SER TRP VAL LEU THR
        195             200             205
        41              46              51
ALA ALA HIS CYS MET ASP GLU SER LYS LYS LEU LEU VAL ARG LEU GLY
    210             215             220
    56              60, 61          65
GLU TYR ASP LEU ARG ARG TRP GLU LYS TRP GLU LEU ASP LEU ASP ILE
225             230             235             240
70              75              80              85
```

FIG. 1

```
LYS GLU VAL PHE VAL HIS PRO ASN TYR SER LYS SER THR THR ASP ASN
            245             250             255
             90              95             100

ASP ILE ALA LEU LEU HIS LEU ALA GLN PRO ALA THR LEU SER GLN THR
            260             265             270
            105             110             115

ILE VAL PRO ILE CYS LEU PRO ASP SER GLY LEU ALA GLU ARG GLU LEU
            275             280             285
            120             125             128ₐ 128ᵦ 128c 129 129ₐ

ASN GLN ALA GLY GLN GLU THR LEU VAL THR GLY TRP GLY TYR HIS SER
    290             295             300
130                 136             141

SER ARG GLU LYS GLU ALA LYS ARG ASN ARG THR PHE VAL LEU ASN PHE
305             310             315                         320
146             149 149ₐ 149ᵦ 149c 149d 150   152                         157

ILE LYS ILE PRO VAL VAL PRO HIS ASN GLU CYS SER GLU VAL MET SER
            325             330             335
            162             167             172

ASN MET VAL SER GLU ASN MET LEU CYS ALA GLY ILE LEU GLY ASP ARG
            340             345             350
            177             182     184 184ₐ 185 186 186ₐ 187

GLN ASP ALA CYS GLU GLY ASP SER GLY GLY PRO MET VAL ALA SER PHE
            355             360             365
            190             195             200

HIS GLY THR TRP PHE LEU VAL GLY LEU VAL SER TRP GLY GLU GLY CYS
    370             375             380
    205             210             215 216 217 219 220

GLY LEU LEU HIS ASN TYR GLY VAL TYR THR LYS VAL SER ARG TYR LEU
385             390             395                         400
221 221ₐ         225             230                         235

ASP TRP ILE HIS GLY HIS ILE ARG ASP LYS GLU ALA PRO GLN LYS SER
            405             410             415
            240             245             250

Trp Ala Pro
       254
```

FIG. 1 (END)

```
Met-Gly-Arg-Pro-Leu-His-Leu-Val-Leu-Leu-Ser-Ala-Ser-Leu-Ala-Gly
 1                5                  10                   15
Leu-Leu-Leu-Leu-Gly-Glu-Ser-Leu-Phe-Ile-Arg-Arg-Glu-Gln-Ala-Asn
              20                  25                  30
Asn-Ile-Leu-Ala-Arg-Val-Thr-Arg-Ala-Asn-Ser-Phe-Leu-Glu-Glu-Met
         35                  40                  45
Lys-Lys-Gly-His-Leu-Glu-Arg-Glu-Cys-Met-Glu-Glu-Thr-Cys-Ser-Tyr
     50                  55                  60
Glu-Glu-Ala-Arg-Glu-Val-Phe-Glu Asp-Ser-Asp-Lys-Thr-Asn-Glu-Phe
 65                  70                  75                  80
Trp-Asn-Lys-Tyr-Lys-Asp-Gly-Asp-Gln-Cys-Glu-Thr-Ser-Pro-Cys-Gln
              85                  90                  95
Asn-Gln-Gly-Lys-Cys-Lys-Asp-Gly-Leu-Gly-Glu-Tyr-Thr-Cys-Thr-Cys
             100                 105                 110
Leu-Glu-Gly-Phe-Glu-Gly-Lys-Asn-Cys-Glu-Leu-Phe-Thr-Arg-Lys-Leu
             115                 120                 125
Cys-Ser-Leu-Asp-Asn-Gly-Asp-Cys-Asp-Gln-Phe-Cys-His-Glu-Glu-Gln
 130                 135                 140
Asn-Ser-Val-Val-Cys-Ser-Cys-Ala-Arg-Gly-Tyr-Thr-Leu-Ala-Asp-Asn
145                 150                 155                 160
Gly-Lys-Ala-Cys-Ile-Pro-Thr-Gly-Pro-Tyr-Pro-Cys-Gly-Lys-Gln-Thr
             165                 170                 175
Leu-Glu-Arg-Arg-Lys-Arg-Ser-Val-Ala-Gln-Ala-Thr-Ser-Ser-Ser-Gly
             180-181-182          185                 190
Glu-Ala-Pro-Asp-Ser-Ile-Thr-Trp-Lys-Pro-Tyr-Asp-Ala-Ala-Asp-Leu
             195                 200                 205
Asp-Pro-Thr-Glu-Asn-Pro-Phe-Asp-Leu-Leu-Asp-Phe-Asn-Gln-Thr-Gln
             210                 215                 220
Pro-Glu-Arg-Gly-Asp-Asn Asn-Leu-Thr-Arg-Ile-Val-Gly-Gly-Gln-Glu
225                 230                 235                 240
                                         16  17  18      20
Cys-Lys-Asp-Gly-Glu-Cys-Pro-Trp-Gln-Ala-Leu-Leu-Ile-Asn-Glu-Glu
             245                 250                 255
             25                  30                  35
Asn-Glu-Gly-Phe-Cys-Gly-Gly-Thr-Ile-Leu-Ser-Glu-Phe-Tyr-Ile-Leu
             260                 265                 270
             40                  45                  50
Thr-Ala-Ala-His-Cys-Leu-Tyr-Gln-Ala-Lys-Arg-Phe-Lys-Val-Arg-Val
             275                 280                 285
  55      57*           60      61a             65
Gly-Asp-Arg-Asn-Thr-Glu-Gln-Glu-Glu-Gly-Gly-Glu-Ala-Val-His-Glu
             290                 295                 300
             70                  75                  80
Val-Glu-Val-Val-Ile-Lys-His-Asn-Arg-Phe-Thr-Lys-Glu-Thr-Tyr-Asp
305                 310                 315                 320
 85                  90                  95                 100
Phe-Asp-Ile-Ala-Val-Leu-Arg-Leu-Lys-Thr-Pro-Ile-Thr-Phe-Arg-Met
             325                 330                 335
```

FIG. 2

```
Asn-Val-Ala-Pro-Ala-Cys-Leu-Pro-Glu-Arg-Asp-Trp-Ala-Glu-Ser-Thr
            340             345             350
      120             124a              130
Leu-Met-Thr-Gln-Lys-Thr-Gly-Ile-Val-Ser-Gly-Phe-Gly-Arg-Thr-His
            355             360             365
131a131b          135             140             145
Glu-Lys-Gly-Arg-Gln-Ser-Thr-Arg-Leu-Lys-Met-Leu-Glu-Val-Pro-Tyr
     370             375             380
            150             155             160
Val-Asp-Arg-Asn-Ser-Cys-Lys-Leu-Ser-Ser-Ser-Phe-Ile-Ile-Thr-Gln
 385             390             395             400
        165             170             175
Asn-Met-Phe-Cys-Ala-Gly-Tyr-Asp-Thr-Lys-Gln-Glu-Asp-Ala-Cys-Gln
                405             410             415
    180             185 185a185b             190
Gly-Asp-Ser-Gly-Gly-Pro-His-Val-Thr-Arg-Phe-Lys-Asp-Thr-Tyr-Phe
            420             425             430
       195*             200             205
Val-Thr-Gly-Ile-Val-Ser-Trp-Gly-Glu-Gly-Cys-Ala-Arg-Lys-Gly-Lys
            435             440             445
      210             215      218 220         223 223a
Tyr-Gly-Ile-Tyr-Thr-Lys-Val-Thr-Ala-Phe-Leu-Lys-Trp-Ile-Asp-Arg
      450             455             460
    225             230             235             240
Ser-Met-Lys-Thr-Arg-Gly-Leu-Pro-Lys-Ala-Lys-Ser-His-Ala-Pro-Glu
 465             470             475             480
                   245             250
Val-Ile-Thr-Ser-Ser-Pro-Leu-Lys
            485
```

FIG. 2 (END)

SEQUENCE LISTING

```
<160> NUMBER OF SEQ ID NOS: 32

<210> SEQ ID NO 1
<211> LENGTH: 419
<212> TYPE: PRT
<213> ORGANISM: Homo sapiens

<400> SEQUENCE: 1

Ala Asn Ser Phe Leu Glu Glu Leu Arg His Ser Ser Leu Glu Arg Glu
1               5                   10                  15

Cys Ile Glu Glu Ile Cys Asp Phe Glu Glu Ala Lys Glu Ile Phe Gln
            20                  25                  30

Asn Val Asp Asp Thr Leu Ala Phe Trp Ser Lys His Val Asp Gly Asp
        35                  40                  45

Gln Cys Leu Val Leu Pro Leu Glu His Pro Cys Ala Ser Leu Cys Cys
    50                  55                  60

Gly His Gly Thr Cys Ile Asp Gly Ile Gly Ser Phe Ser Cys Asp Cys
65                  70                  75                  80

Arg Ser Gly Trp Glu Gly Arg Phe Cys Gln Arg Glu Val Ser Phe Leu
                85                  90                  95

Asn Cys Ser Leu Asp Asn Gly Gly Cys Thr His Tyr Cys Leu Glu Glu
            100                 105                 110

Val Gly Trp Arg Arg Cys Ser Cys Ala Pro Gly Tyr Lys Leu Gly Asp
        115                 120                 125

Asp Leu Leu Gln Cys His Pro Ala Val Lys Phe Pro Cys Gly Arg Pro
    130                 135                 140

Trp Lys Arg Met Glu Lys Lys Arg Ser His Leu Lys Arg Asp Thr Glu
145                 150                 155                 160

Asp Gln Glu Asp Gln Val Asp Pro Arg Leu Ile Asp Gly Lys Met Thr
                165                 170                 175

Arg Arg Gly Asp Ser Pro Trp Gln Val Val Leu Leu Asp Ser Lys Lys
            180                 185                 190

Lys Leu Ala Cys Gly Ala Val Leu Ile His Pro Ser Trp Val Leu Thr
        195                 200                 205

Ala Ala His Cys Met Asp Glu Ser Lys Lys Leu Leu Val Arg Leu Gly
    210                 215                 220

Glu Tyr Asp Leu Arg Arg Trp Glu Lys Trp Glu Leu Asp Leu Asp Ile
225                 230                 235                 240

Lys Glu Val Phe Val His Pro Asn Tyr Ser Lys Ser Thr Thr Asp Asn
                245                 250                 255

Asp Ile Ala Leu Leu His Leu Ala Gln Pro Ala Thr Leu Ser Gln Thr
            260                 265                 270

Ile Val Pro Ile Cys Leu Pro Asp Ser Gly Leu Ala Glu Arg Glu Leu
        275                 280                 285
```

```
Asn Gln Ala Gly Gln Glu Thr Leu Val Thr Gly Trp Gly Tyr His Ser
            290                 295                 300
Ser Arg Glu Lys Glu Ala Lys Arg Asn Arg Thr Phe Val Leu Asn Phe
305                 310                 315                 320
Ile Lys Ile Pro Val Val Pro His Asn Glu Cys Ser Glu Val Met Ser
                325                 330                 335
Asn Met Val Ser Glu Asn Met Leu Cys Ala Gly Ile Leu Gly Asp Arg
            340                 345                 350
Gln Asp Ala Cys Glu Gly Asp Ser Gly Gly Pro Met Val Ala Ser Phe
        355                 360                 365
His Gly Thr Trp Phe Leu Val Gly Leu Val Ser Trp Gly Glu Gly Cys
    370                 375                 380
Gly Leu Leu His Asn Tyr Gly Val Tyr Thr Lys Val Ser Arg Tyr Leu
385                 390                 395                 400
Asp Trp Ile His Gly His Ile Arg Asp Lys Glu Ala Pro Gln Lys Ser
                405                 410                 415
Trp Ala Pro
```

<210> SEQ ID NO 2
<211> LENGTH: 10
<212> TYPE: PRT
<213> ORGANISM: Homo sapiens

<400> SEQUENCE: 2

```
Asp Phe Leu Ala Glu Gly Gly Gly Val Arg
1               5                   10
```

<210> SEQ ID NO 3
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 3
gactttctag ctgaaggagg aggcgtgcgg ctcattgatg ggaagatgac c        51

<210> SEQ ID NO 4
<211> LENGTH: 50
<212> TYPE: DNA
<213> ORGANISM: Artificial sequence
<220> FEATURE:
<223> OTHER INFORMATION: synthetic oligonucleotide

<400> SEQUENCE: 4
cacgctcctc cttcagctag aaagtctcgt ttcaggtgac tgcgcttctt            50

<210> SEQ ID NO 5
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 5
gaaggaggag gcgtgcgctc ttcggcggga agatgaccag gcg                43

<210> SEQ ID NO 6
<211> LENGTH: 41
<212> TYPE: DNA
<213> ORGANISM: Artificial sequence -continued
<220> FEATURE:
<223> OTHER INFORMATION: synthetic oligonucleotide

<400> SEQUENCE: 6
cgcctggtca tcttcccgcc gaagagccgc acgcctcctt c        41

<210> SEQ ID NO 7
<211> LENGTH: 44
<212> TYPE: DNA
<213> ORGANISM: Artificial sequence
<220> FEATURE:
<223> OTHER INFORMATION: synthetic oligonucleotide

<400> SEQUENCE: 7
gaaggaggag gcgtgcggtc cattggcggg aagatgacca ggcg        44

<210> SEQ ID NO 8
<211> LENGTH: 44
<212> TYPE: DNA
<213> ORGANISM: Artificial sequence
<220> FEATURE:
<223> OTHER INFORMATION: synthetic oligonucleotide

<400> SEQUENCE: 8
cgcctggtca tcttcccgcc aatggaccgc acgcctcctc cttc        44

<210> SEQ ID NO 9
<211> LENGTH: 44
<212> TYPE: DNA
<213> ORGANISM: Artificial sequence
<220> FEATURE:
<223> OTHER INFORMATION: synthetic oligonucleotide

<400> SEQUENCE: 9
gaaggaggag gcgtgcgggc cattggcggg aagatgacca ggcg        44

<210> SEQ ID NO 10
<211> LENGTH: 44
<212> TYPE: DNA
<213> ORGANISM: Artificial sequence
<220> FEATURE:
<223> OTHER INFORMATION: synthetic oligonucleotide

<400> SEQUENCE: 10
cgcctggtca tcttcccgcc aatggcccgc acgcctcctc cttc        44

<210> SEQ ID NO 11
<211> LENGTH: 44
<212> TYPE: DNA
<213> ORGANISM: Artificial sequence
<220> FEATURE:
<223> OTHER INFORMATION: synthetic oligonucleotide

<400> SEQUENCE: 11
gaaggaggag gcgtgcggct cattggcggg aagatgacca ggcg        44

<210> SEQ ID NO 12
<211> LENGTH: 43
<212> TYPE: DNA
<213> ORGANISM: Artificial sequence
<220> FEATURE:
<223> OTHER INFORMATION: synthetic oligonucleotide

<400> SEQUENCE: 12
cgcctggtca tcttcccgcc aatgagccgc acgctcctcc ttc        43

<210> SEQ ID NO 13
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 13
agcgcagtca cctgaaacga caagtagatc cgcggctcat                    40

<210> SEQ ID NO 14
<211> LENGTH: 40
<212> TYPE: DNA
<213> ORGANISM: Artificial sequence
<220> FEATURE:
<223> OTHER INFORMATION: synthetic oligonucleotide

<400> SEQUENCE: 14
atgagccgcg gatctacttg tcgtttcagg tgactgcgct                    40

<210> SEQ ID NO 15
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 15
gactttctag ctgaaggagg aggcgtgagg atcgtgggag gccaggaatg c       51

<210> SEQ ID NO 16
<211> LENGTH: 51
<212> TYPE: DNA
<213> ORGANISM: Artificial sequence
<220> FEATURE:
<223> OTHER INFORMATION: synthetic oligonucleotide

<400> SEQUENCE: 16
cacgcctcct ccttcagcta gaaagtccct cttcctgcgt tccagggtct g       51

<210> SEQ ID NO 17
<211> LENGTH: 55
<212> TYPE: DNA
<213> ORGANISM: Artificial sequence
<220> FEATURE:
<223> OTHER INFORMATION: synthetic oligonucleotide

<400> SEQUENCE: 17
gactttctag ctgaaggagg aggcgtgagg atcttcggag gccaggaatg caagg   55

<210> SEQ ID NO 18
<211> LENGTH: 60
<212> TYPE: DNA
<213> ORGANISM: Artificial sequence
<220> FEATURE:
<223> OTHER INFORMATION: synthetic oligonucleotide

<400> SEQUENCE: 18
gaagatcctc acgcctcctc cttcagctag aaagtccctc ttcctgcgtt ccagggtctg   60

<210> SEQ ID NO 19
<211> LENGTH: 35
<212> TYPE: DNA
<213> ORGANISM: Artificial sequence
<220> FEATURE:
<223> OTHER INFORMATION: synthetic oligonucleotide

<400> SEQUENCE: 19
ggaggaggcg tgagggccgt gggaggccag gaatg                               35

<210> SEQ ID NO 20
<211> LENGTH: 35
<212> TYPE: DNA
<213> ORGANISM: Artificial sequence
<220> FEATURE:
<223> OTHER INFORMATION: synthetic oligonucleotide

<400> SEQUENCE: 20
cattcctggc ctcccacggc cctcacgcct cctcc                              35

<210> SEQ ID NO 21
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 21
ggaggaggcg tgagggcctt cggaggccag gaatgcaag                           39

<210> SEQ ID NO 22
<211> LENGTH: 39
<212> TYPE: DNA
<213> ORGANISM: Artificial sequence
<220> FEATURE:
<223> OTHER INFORMATION: synthetic oligonucleotide

<400> SEQUENCE: 22
cttgcattcc tggcctccga aggccctcac gcctcctcc                           39

<210> SEQ ID NO 23
<211> LENGTH: 488
<212> TYPE: PRT
<213> ORGANISM: Homo sapiens

<400> SEQUENCE: 23

```
Met Gly Arg Pro Leu His Leu Val Leu Leu Ser Ala Ser Leu Ala Gly
1               5                   10                  15

Leu Leu Leu Leu Gly Glu Ser Leu Phe Ile Arg Arg Glu Gln Ala Asn
            20                  25                  30

Asn Ile Leu Ala Arg Val Thr Arg Ala Asn Ser Phe Leu Glu Glu Met
        35                  40                  45

Lys Lys Gly His Leu Glu Arg Glu Cys Met Glu Glu Thr Cys Ser Tyr
    50                  55                  60

Glu Glu Ala Arg Glu Val Phe Glu Asp Ser Asp Lys Thr Asn Glu Phe
65                  70                  75                  80

Trp Asn Lys Tyr Lys Asp Gly Asp Gln Cys Glu Thr Ser Pro Cys Gln
                85                  90                  95

Asn Gln Gly Lys Cys Lys Asp Gly Leu Gly Glu Tyr Thr Cys Thr Cys
            100                 105                 110

Leu Glu Gly Phe Glu Gly Lys Asn Cys Glu Leu Phe Thr Arg Lys Leu
        115                 120                 125

Cys Ser Leu Asp Asn Gly Asp Cys Asp Gln Phe Cys His Glu Glu Gln
    130                 135                 140

Asn Ser Val Val Cys Ser Cys Ala Arg Gly Tyr Thr Leu Ala Asp Asn
145                 150                 155                 160
```

```
Gly Lys Ala Cys Ile Pro Thr Gly Pro Tyr Pro Cys Gly Lys Gln Thr
                165                 170                 175
Leu Glu Arg Arg Lys Arg Ser Val Ala Gln Ala Thr Ser Ser Ser Gly
            180                 185                 190
Glu Ala Pro Asp Ser Ile Thr Trp Lys Pro Tyr Asp Ala Ala Asp Leu
        195                 200                 205
Asp Pro Thr Glu Asn Pro Phe Asp Leu Leu Asp Phe Asn Gln Thr Gln
    210                 215                 220
Pro Glu Arg Gly Asp Asn Asn Leu Thr Arg Ile Val Gly Gly Gln Glu
225                 230                 235                 240
Cys Lys Asp Gly Glu Cys Pro Trp Gln Ala Leu Leu Ile Asn Glu Glu
                245                 250                 255
Asn Glu Gly Phe Cys Gly Gly Thr Ile Leu Ser Glu Phe Tyr Ile Leu
            260                 265                 270
Thr Ala Ala His Cys Leu Tyr Gln Ala Lys Arg Phe Lys Val Arg Val
        275                 280                 285
Gly Asp Arg Asn Thr Glu Gln Glu Glu Gly Gly Glu Ala Val His Glu
    290                 295                 300
Val Glu Val Val Ile Lys His Asn Arg Phe Thr Lys Glu Thr Tyr Asp
305                 310                 315                 320
Phe Asp Ile Ala Val Leu Arg Leu Lys Thr Pro Ile Thr Phe Arg Met
                325                 330                 335
Asn Val Ala Pro Ala Cys Leu Pro Glu Arg Asp Trp Ala Glu Ser Thr
            340                 345                 350
Leu Met Thr Gln Lys Thr Gly Ile Val Ser Gly Phe Gly Arg Thr His
        355                 360                 365
Glu Lys Gly Arg Gln Ser Thr Arg Leu Lys Met Leu Glu Val Pro Tyr
    370                 375                 380
Val Asp Arg Asn Ser Cys Lys Leu Ser Ser Ser Phe Ile Ile Thr Gln
385                 390                 395                 400
Asn Met Phe Cys Ala Gly Tyr Asp Thr Lys Gln Glu Asp Ala Cys Gln
                405                 410                 415
Gly Asp Ser Gly Gly Pro His Val Thr Arg Phe Lys Asp Thr Tyr Phe
            420                 425                 430
Val Thr Gly Ile Val Ser Trp Gly Glu Gly Cys Ala Arg Lys Gly Lys
        435                 440                 445
Tyr Gly Ile Tyr Thr Lys Val Thr Ala Phe Leu Lys Trp Ile Asp Arg
    450                 455                 460
Ser Met Lys Thr Arg Gly Leu Pro Lys Ala Lys Ser His Ala Pro Glu
465                 470                 475                 480
Val Ile Thr Ser Ser Pro Leu Lys
                485

<210> SEQ ID NO 24
<211> LENGTH: 12
<212> TYPE: PRT
<213> ORGANISM: Artificial Sequence
<220> FEATURE:
<223> OTHER INFORMATION: synthetic peptide

<400> SEQUENCE: 24

Asp Thr Glu Asp Gln Glu Asp Gln Val Asp Pro Arg
1               5                   10

<210> SEQ ID NO 25
<211> LENGTH: 6
```

```
<212> TYPE: PRT
<213> ORGANISM: Homo sapiens

<400> SEQUENCE: 25

Leu Thr Arg Ile Val Gly
1               5

<210> SEQ ID NO 26
<211> LENGTH: 13
<212> TYPE: PRT
<213> ORGANISM: Artificial Sequence
<220> FEATURE:
<223> OTHER INFORMATION: mutant peptide

<400> SEQUENCE: 26

Asp Phe Leu Ala Glu Gly Gly Gly Val Arg Ile Val Gly
1               5                   10

<210> SEQ ID NO 27
<211> LENGTH: 13
<212> TYPE: PRT
<213> ORGANISM: Artificial Sequence
<220> FEATURE:
<223> OTHER INFORMATION: mutant peptide

<400> SEQUENCE: 27

Asp Phe Leu Ala Glu Gly Gly Gly Val Arg Ile Phe Gly
1               5                   10

<210> SEQ ID NO 28
<211> LENGTH: 13
<212> TYPE: PRT
<213> ORGANISM: Artificial Sequence
<220> FEATURE:
<223> OTHER INFORMATION: mutant peptide

<400> SEQUENCE: 28

Asp Phe Leu Ala Glu Gly Gly Gly Val Arg Ala Val Gly
1               5                   10

<210> SEQ ID NO 29
<211> LENGTH: 13
<212> TYPE: PRT
<213> ORGANISM: Artificial Sequence
<220> FEATURE:
<223> OTHER INFORMATION: mutant peptide

<400> SEQUENCE: 29

Asp Phe Leu Ala Glu Gly Gly Gly Val Arg Ala Phe Gly
1               5                   10

<210> SEQ ID NO 30
<211> LENGTH: 5
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: D isomer
<220> FEATURE:
<221> NAME/KEY: misc_feature
<222> LOCATION: (4)..(4)
<223> OTHER INFORMATION: includes a CH3Cl group

<400> SEQUENCE: 30

Phe Phe Arg Cys Lys
1               5
```

-continued

```
<210> SEQ ID NO 31
<211> LENGTH: 4
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (1)..(1)
<223> OTHER INFORMATION: includes a benzyl-CO group
<220> FEATURE:
<221> NAME/KEY: misc_feature
<222> LOCATION: (2)..(3)
<223> OTHER INFORMATION: gamma-OR present between amino acids 2 and 3

<400> SEQUENCE: 31

Ile Gln Gly Arg
1

<210> SEQ ID NO 32
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: misc_feature
<222> LOCATION: (11)..(11)
<223> OTHER INFORMATION: Xaa is a non-acidic amino acid excluding Gly
<220> FEATURE:
<221> NAME/KEY: misc_feature
<222> LOCATION: (12)..(12)
<223> OTHER INFORMATION: Xaa is a non-acidic amino acid excluding Pro
<220> FEATURE:
<221> NAME/KEY: misc_feature
<222> LOCATION: (13)..(13)
<223> OTHER INFORMATION: Xaa is a basic amino acid excluding Arg

<400> SEQUENCE: 32

Asp Phe Leu Ala Glu Gly Gly Gly Val Arg Xaa Xaa Xaa
1               5                   10
```

THROMBIN-CLEAVABLE CHIMERIC PROTEINS

This application if a national stage application of the PCT/EP02/12191 application, filed Oct. 18, 2002, which claims the benefit of the FRANCE 01/13492 application, filed Oct. 19, 2001.

The present invention relates to thrombin-cleavable chimeric proteins, in particular to proteins derived from human protein C and from human factor X, and to therapeutic uses thereof.

Protein C (hereinafter referred to as PC) is an essential factor of a major mechanism for regulating clotting, named "anticoagulant pathway". The active form of PC (activated protein C, hereinafter referred to as PCa) is a serine protease which, when associated with another cofactor (protein S), degrades two factors of the clotting cascade essential to the massive generation of thrombin: factors Va and VIIIa. The destruction of these factors negatively regulates the amount of thrombin formed, resulting in an anticoagulant effect. Factor X (hereinafter referred to as FX) is an essential factor of the clotting cascade. The activated form of FX (activated factor X, hereinafter referred to as FXa) is the only serine protease which, associated with its cofactor (clotting factor Va), is capable of activating prothrombin to thrombin.

The PC is a 62 000 Da glycoprotein synthesized in the liver. Before it is secreted into the plasma, its polypeptide chain undergoes several post-translational maturations in order to become a functional proenzyme. These maturations comprise cleavage of the pre- and pro-peptide, γ-carboxylation of the first nine glutamates of the amino-terminal region, β-hydroxylation of the aspartate at position 71, glycosylation of 4 residues distributed along the sequence and excision of the $Lys^{156}$-$Arg^{157}$ doublet, separating the (amino-terminal) light chain and the (carboxy-terminal) heavy chain, and result in the mature form of PC. Due to an incomplete excision of the $Lys^{156}$-$Arg^{157}$ doublet during maturation by the hepatic cells, 10 to 20% of plasma PC remains in a single-stranded form. However, the major plasma form consists of two polypeptide chains which are connected by a disulphide bridge. The 21 000 Da light chain is composed of 155 amino acids, comprising a small domain carrying the γ-carboxyglutamic acids, which is followed by two *Epidermal Growth Factor* (EGF)-type domains. The 41 000 Da heavy chain is composed of 262 amino acids and represents the future catalytic domain, classified in the SA class of the serine protease family (SHEN and DAHLBACK, Handbook of proteolytic enzymes: Protein C. Barrett, A. J., Rawlings, N. D., Woessner J. F., eds. Academic Press, Orlando, Fla. 1998).

FX is a 59 000 Da glycoprotein synthesized in the liver. Before it is secreted into the plasma, its polypeptide chain undergoes several post-translational maturations in order to become a functional proenzyme. These maturations comprise cleavage of the pre-and pro-peptide, γ-carboxylation of the first eleven glutamates of the amino-terminal region, β-hydroxylation of the aspartate at position 103, glycosylation of at least 5 residues (including 4 on the activation peptide) and excision of the $Arg_{180}$-$Lys_{181}$-$Arg_{182}$ tripeptide. Unlike PC, virtually all the mature FX circulating in the plasma is in double-stranded form, with the strands connected by a disulphide bridge. The 16 900 Da light chain is composed of 139 amino acids, comprising a small domain carrying the γ-carboxyglutamic acids, which is followed by two EGF domains. The 42 100 Da heavy chain is composed of 306 amino acids and represents the future catalytic domain, classified in the SA class of the serine protease family (STENFLO, Handbook of proteolytic enzymes: Factor X. Barrett, A. J., Rawlings, N. D., Woessner J. F., eds. Academic Press, Orlando, Fla. 1998).

Like most serine protease precursors, PC and FX are zymogens lacking catalytic activity. The activation thereof is the result of proteolytic cleavage in their heavy chains. In PC, this cleavage takes place at the N-terminal end of the heavy chain, releasing a 12 amino acid "activation" peptide. In FX, this cleavage takes place between the $Arg_{234}$ and $Ile_{235}$ residues, also releasing an "activation" peptide, of 52 amino acids.

The polypeptide sequence of the heavy chain and of the light chain of the mature form of PC is represented in FIG. 1, and in the attached sequence listing under the number SEQ ID NO: 1. The main regions of PC are indicated on the sequence of FIG. 1. The heavy chain is underlined. The $Lys^{156}$-$Arg^{157}$ doublet is represented in bold characters. The activation peptide is boxed.

The polypeptide sequence of the heavy chain and of the light chain of the mature form of FX is represented in FIG. 2, and in the attached sequence listing under the number SEQ ID NO: 23. The main regions of FX are indicated on the sequence of FIG. 2. The heavy chain is underlined. The $Arg^{180}$-$Lys^{181}$-$Arg^{182}$ triplet is represented in bold characters. The activation peptide is boxed.

To locate the amino acid residues relative to the sequence of PC, various numbering systems may be used, and in particular:
  a system of numbering with reference to the sequence deduced from the cDNA of PC (BECKMAN et al., Nucleic Acid Res., 13, 5233-5247, 1995); this numbering is represented in FIG. 1, under the peptide sequence;
  a system of numbering the residues of the heavy chain of PC with reference to the numbering of the residues of the catalytic domain of chymotrypsin (MATHERS et al., EMBO J., 15, 6822-6831, 1996). This numbering, generally used for serine proteases, is based on the topological similarities which exist between these enzymes, which greatly facilitates the comparison thereof. This numbering is represented in italics in FIG. 1 under the numbering with reference to the cDNA sequence.

To locate the amino acid residues relative to the sequence of FX, these various numbering systems may also be used, and in particular:
  the system of numbering with reference to the sequence deduced from the cDNA of FX (MESSIER et al., Gene, 99, 291-294, 1991); this numbering is represented in FIG. 2, under the peptide sequence;
  the system of numbering the residues of the heavy chain of FX with reference to the numbering of the residues of the catalytic domain of chymotrypsin (PADMANABHAN et al., J. Mol. Biol., 232, 1-20, 1993); this numbering is represented in italics on FIG. 2, under the numbering with reference to the cDNA sequence.

For example, if the numbering is done with reference to the mature form of PC, the Arg and Leu residues which border the proteolytic cleavage site giving rise to PCa are identified by the positions $Arg^{169}$ and $Leu^{170}$; if the numbering is done with reference to the catalytic domain of chymotrypsin, these same residues are identified by the positions $Arg^{15}$ and $Leu^{16}$. Similarly, if the numbering is done with reference to the mature form of FX, the Arg and Ile residues which border the proteolytic cleavage site giving rise to FXa are identified by the positions $Arg^{234}$ and $Ile^{235}$; if the numbering is done with reference to the catalytic domain of chymotrypsin, these same residues are identified by the positions $Arg^{15}$ and $Ile^{16}$.

Another universal numbering system also used refers to the proteolytic cleavage site. The positions of the amino acids are given in increasing order from this cleavage site. The positions upstream of the site are identified by P, and the positions downstream of the site by P'. Thus, in the case of PC, $P_{12}$ represents the N-terminal amino acid of the activation peptide (the furthest from the cleavage site), and $P_1$ represents the C-terminal amino acid of the activation peptide; $P_1'$ represents the N-terminal amino acid of PCa.

Activation of PC is the result of it being cleaved by thrombin complexed with a membrane-bound cofactor, thrombomodulin, present at the surface of the vascular endothelium. In the absence of thrombomodulin, activation of PC by thrombin is approximately 1 000 times slower and generates only a negligible amount of PCa.

Given the cross section of the vessel, the amount of thrombomodulin molecules per volume irrigated is much higher in the microcirculation than in the large calibre vessels. As a result of this, in the presence of thrombin, PCa generation is rapid in the microcirculation but slow in the large calibre vessels. The physiological role of the anticoagulant pathway is therefore limited to the microcirculation.

The importance of the anticoagulant pathway is underlined by the seriousness of genetic or acquired deficiencies in the proteins participating in this system; a deficiency in PC or in protein S or resistance of factor Va to inactivation by PCa can be identified in more than 30% of thrombotic accidents (AI-ACH et al., Seminars in Haematology, 34, 205-217, 1997). Transgenic mice in which the PC gene has been inactivated (JALBERT et al., 0.1. Clin. Invest. 102 (8), 1481-1488, 1998) or in which the thrombomodulin gene is nonfunctional (WEILER-GUETTLER et al., J. Clin. Invest., 101, 1983-1991, 1998) exhibit clotting abnormalities, objectified in particular by the appearance of fibrin deposits in various organs.

Various studies have shown that PC has pleiotropic biological activity: not only antithrombotic activity (TAYLOR et al., J. Clin. Invest., 79, 918-925, 1987; GRUBER et al., Blood, 73, 639-642, 1989; Circulation, 82, 578-585, 1990; CHESEBRO et al., Circulation, 86, III100-110, 1992; HANSON et al., J. Clin. Invest., 92, 2003-2012, 1993; ARNLJOTS et al., Thromb. Haemost., 72, 415-420, 1994; SAKAMOTO et al., Circulation, 90, 427-432, 1994; JANG et al., Circulation, 92, 3041-3050, 1995; KURZ et al., Blood, 89, 534-540, 1997; GRESELE et al., J. Clin. Invest., 101, 667-676, 1998; MIIZUTANI et al., Blood, 95, 3781-3787, 2000; BERNARD et al., N. Engl. J. Med., 344, 699-709, 2001), but also anti-inflammatory activity (ESMON, Biochim. Biophys. Acta., 1477, 349-360, 2000), anti-apoptotic activity (JOYCE et al., J. Biol. Chem., 276, 11199-11203, 2001) and pro-fibrinolytic activity (COMP & ESMON, J. Clin. Invest., 68, 1221-1228, 1981; REZAIE, J. Biol. Chem., 276, 15567-15570, 2001). This pharmacological spectrum makes it an excellent candidate for the treatment of thrombotic disease in general, since, in this physiopathology, there is often an inflammatory reaction, and sometimes cell death, associated with this thrombotic process.

In addition, the inducible mechanism of PC activation makes it an auto regulated antithrombotic, the action of which is targeted on the thrombus, thus limiting the haemorrhagic risk inherent to conventional antithrombotics.

The administration of PC concentrates has proved to be beneficial in the treatment of homozygous genetic PC deficiencies and also acquired deficiencies such as meningococcal infections associated with purpura fulminans (GERSON et al., Pediatrics, 91, 418-422, 1993; OKAJIMA et al., Am. J. Hematol., 33, 277-278, 1990; DREYFUS et al., N. Engl. J. Med., 325, 1565-1568, 1991; MANCO-JOHNSON & NUSS, Am. J. Hematol., 40, 69-70, 1992; RINTALA et al., Lancet, 347, 1767, 1996; SMITH et al., Lancet, 350, 1590-1593, 1997; WHITE et al., Blood, 96, 3719-3724, 2000). This substitutive therapy makes it possible to correct disorders associated with these deficiencies by reconstituting a stock of circulating PC.

However, the use of PC concentrates as an antithrombotic treatment in the case of large vessel, arterial or venous thromboses cannot be envisaged. As mentioned above, the amount of thrombomodulin available constitutes a limiting factor; even with saturating concentrations of PC, the activation thereof remains too slow to obtain an adequate therapeutic effect.

In order to extend the biological activity of the PC anticoagulant pathway to the entire vascular territory, the direct use of PCa has been proposed. This solution has proved to be effective (BERNARD et al., N. Engl. J. Med., 344, 699-709, 2001) but its use is limited by the very short half-life (approximately 30 min) of PCa in the circulation. In fact, like most activated serine proteases, PCa is rapidly neutralized by inhibitors (serpins) present in the plasma. The therapeutic effect can therefore only be obtained with continuous infusion.

One of the solutions envisaged in order to overcome this limitation consists in making modifications to PCa so as to increase its resistance to plasma inhibitors. However, another problem is posed by the fact that the use of PCa does not make it possible to benefit from a major advantage of PC, namely activation inducible by the presence of thrombin. A PCa which is resistant to inhibitors, and the formation of which cannot be regulated, has the drawbacks of conventional antithrombotics, namely an anticoagulant action not limited to the thrombotic area, and the potential haemorrhagic risk which ensues therefrom.

Another approach which has been proposed consists in seeking to modify PC in order to make it directly activatable by thrombin in the absence of thrombomodulin, with the aim of enabling the formation of PCa throughout the thrombus, and not only in the immediate vicinity of the vascular endothelium.

Thus, U.S. Pat. No. 5,453,373 describes various PC derivatives:
- the derivative named F167 results from substituting the Asp residue at position 167 of the mature form of PC (position $P_3$ of the activation peptide) with a Phe residue; this derivative is activated by thrombin in the absence of thrombomodulin with a rate 12 times greater than that of native PC;
- the derivative named LIN results from substituting Asp residue at position 172 of the mature form of PC (position $P_3'$ relative to the proteolytic cleavage site) with an Asn residue; this derivative is activated by thrombin in the absence of thrombomodulin with a rate 4 times greater than that of native PC;
- the derivative named FLIN results from substituting the Asp residue at position 167 of the mature form of PC with a Phe residue, and substituting the Asp residue at position 172 of the mature form of PC with an Asn residue; this derivative is activated by thrombin in the absence of thrombomodulin with a rate 30 times greater than that of native PC;
- the derivatives named Q313 and Q329 result, respectively, from substituting the Asn residue at position 313 or the Asn residue at position 329 of the mature form of PC with a Gln residue; these modifications were carried out so as to delete glycosylation sites at these Asn residues, in order to increase the anticoagulant activity of PCa. The derivative Q313 is activated by thrombin with a rate 2 times greater than that of native PC; its anticoagulant activity is 1.8 times greater than that of PCa; the derivative Q329 is activated by thrombin less rapidly that native PC;

the derivative named Q3Q9 and Q329 results from substituting the Asn residue at position 313 and the Asn residue at position 329 of the mature form of PC with Gln residues; this derivative is activated by thrombin in the absence of thrombomodulin with a rate 3.3 times greater, than that of native PC.

The derivatives named FLIN-Q313 and FLIN-Q3Q9 combine these various modifications; they are, respectively, activated by thrombin alone, at a rate 61 times and 84 times greater than that of native PC. These activation rates remain, however, much lower than that of native PC in the presence of thrombomodulin.

The inventors have investigated other modifications of PC which would make it possible to more significantly increase the rate of activation thereof by thrombin independently of thrombomodulin.

They have thus demonstrated two types of modification which promote an acceleration of PC activation by thrombin (under physiological conditions and in the absence of thrombomodulin). In addition, combining these modifications makes it possible to obtain modified PCs, the activation of which in the absence of thrombomodulin is up to 500 times more rapid than that of native PC under the same conditions, and produces modified PCas, the plasma half-life of which is longer than that of native PCa.

A first category of modifications concerns the activation peptide: the inventors found that replacing this peptide with amino acids $P_{10}$ to $P_1$ of fibrinopeptide A (FpA) of fibrinogen (numbered with reference to the proteolytic cleavage site) made it possible to obtain an activation rate 40 times greater than that of normal PC expressed and characterized under the same conditions (in comparison, the derivative F167 described in U.S. Pat. No. 5,453,373, which carries an Asp→Phe substitution at position $p_3$ of the activation peptide, is activated by thrombin only 12 times more rapidly that native PC).

Blood clotting results from a cascade of enzymatic reactions, the ultimate step of which is the generation of thrombin, which induces the formation of a clot able to seal the vascular opening. Most of these reactions involve the proteolytic activation of an inactive zymogen to active serine protease. This cascade of reactions is conventionally divided into two pathways termed: "intrinsic pathway" and "tissue factor pathway", or "extrinsic pathway", depending on whether activation of FX results from it being cleaved with factor IXa or factor VIIa. These pathways therefore converge towards the activation of FX to FXa. FXa is one of the key clotting enzymes since the binding thereof to its cofactor, factor Va, forms the prothrombinase complex, which activates prothrombin to thrombin.

A qualitative or quantitative deficiency in one of the proteins involved in clotting leads to often severe thrombotic or haemorrhagic manifestations, possibly threatening the vital progNOSis. In this context, mention will in particular be made of haemophilia A and B, which result, respectively, from a deficiency in factor VIII or in factor IX.

Treatments for haemophilia proposed at the current time are either treatments of the substitutive type or treatments based on the use of one or more molecules which bypass the deficient step (HEDNER, Thromb. Haemost., 82, 531-539, 1999).

The main drawback of substitutive treatment lies in the potential antigenicity of the injected molecule, which may be seen as foreign by the recipient's immune system. The development of neutralizing allo antibodies directed against the factor used is a serious complication of substitutive treatment which, little by little, makes it ineffective. The main drawback of the "bypass" treatments currently available or undergoing trial is the absence of autoregulation (in particular the absence of localization and/or autoamplification of the production of thrombin). They may lead to rare but serious side effects: anaphylactic shocks and thrombotic accidents (myocardial infarction, disseminated intravascular coagulation).

It therefore appears to be desirable to have available a treatment which would not have these drawbacks. With this aim, the inventors have investigated thrombin-activatable FX derivatives which would make it possible not only to bypass the deficient steps of the clotting cascade, but also to re-establish autoamplification of thrombin generation. The activated form of this FX derivative (FXa*) would in fact be capable (in combination with factor Va) of forming a functional prothrombinase complex and therefore of activating prothrombin to thrombin. In turn, thrombin would activate further FX derivative molecules.

The inventors have thus brought to FX modifications of the same type than those mentioned above for PC. They found that replacing the activation peptide of FX with amino acids $P_{10}$ to $P_1$ of fibrinopeptide A (SEQ ID NO:2) allows to obtain a modified FX that is activatable by thrombin, unlike normal FX.

It therefore appears that replacing the native activation peptide of a thrombin-activatable zymogen with FpA, or with a peptide comprising at least amino acids $P_{10}$ to $P_1$ thereof, makes it possible to increase the rate of activation of this zymogen. In addition, it appears to be possible to construct thrombin-cleavable proteins from zymogens activatable by another serine protease, or even from any polypeptides, by placing at their N-terminal end at least amino acids $P_1'$, $P_2'$ and $P_3'$ of a cleavage site for thrombin, preceded by a peptide comprising at least amino acids $P_{10}$ to $P_1$ of fibrinopeptide A (SEQ ID NO:2). Amino acids which can be used at positions $P_1'$, $P_2'$ and $P_3'$ to constitute a site for cleavage by thrombin are known in themselves; they are, for example, described by DAWSON et al. (J. Biol. Chem., 269, 15989-15992, 1994) in US Pat. No. 5 688 664 or by LE BONNIEC et al. (Biochemistry, 35, 7114-7122, 1996).

On the other hand, although it was considered in the prior art that the presence of a proline residue at position $P_2$ of the cleavage site was necessary for an optimal cleavage by thrombin (cf. in particular DAWSON et al. and U.S. Pat. No. 5,688, 664, cited above), the present invention provides thrombin-cleavable proteins in which the residue at position $P_2$ is a valine. It is supposed that this residue, and also the phenylalanine at position $P_9$ and the glutamate at position $P_6$ of FpA, would allow the use of an additional binding site on thrombin, not used for cleaving normal PC.

The subject of the present invention is a thrombin-cleavable chimeric protein comprising at its N-terminal end an activation peptide followed by amino acids $P_1'$-$P_2'$-$P_3'$ of a cleavage site for thrombin, characterized in that said activation peptide is a fibrinopeptide A, or a portion thereof, comprising at least amino acids $P_{10}$ to $P_1$ of said fibrinopeptide A (SEQ ID NO:2); with the exclusion of a chimeric protein in which $P_1'$-$P_2'$-$P_3'$ represents the sequence Gly-Pro-Arg.

A subject of the present invention is a chimeric protein comprising a thrombin-cleavable sequence $P_{10}P_9P_8P_7P_6P_5P_4P_3P_2P_1P_1'P_2'P_3'$ (SEQ ID NO:32), characterized in that said sequence is an artificial sequence comprising amino acids $P_{10}$ to $P_1$ of fibrinopeptide A (SEQ ID NO:2) and amino acids $P_1'$-$P_2'$-$P_3'$ of a cleavage site for thrombin other than that of the alpha chain of fibrinogen.

According to a preferred embodiment of the present invention, said chimeric protein is derived from the zymogen of a serine protease by replacing the activation peptide of said zymogen with fibrinopeptide A, or a portion thereof, comprising at least amino acids $P_{10}$ to $P_1$ (SEQ ID NO:2) of said fibrinopeptide A. Advantageously, said zymogen is PC or FX.

To obtain a chimeric protein of the present invention, it is possible to envisage using of the FpA (or at least amino acids $P_{10}$-$P_1$ (SEQ ID NO:2) thereof) of any animal species, the sequence of FpA being very conserved from one species to another, in particular with regard to the phenylalanine at position $P_9$, the glutamate at position $P_6$ and the valine at position $P_2$. However, for the production of chimeric proteins, for example of PC or FX derivatives, intended to be used in human medicine, use will preferably be made of human FpA, or the peptide sequence DFLAEGGGVR (SEQ ID NO: 2), corresponding to amino acids $P_{10}$ to $P_1$ of human FpA. These peptides in fact have the advantage of being potentially relatively nonimmunogenic since they are naturally exposed in circulating fibrinogen.

As indicated above, many $P_1'$-$P_2'$-$P_3'$ sequences which allow cleavage by thrombin are known in themselves; these are in particular the $P_1'$-$P_2'$-$P_3'$ sequences of the cleavage sites for thrombin of proteins which exist naturally in the form of thrombin-activatable zymogens. These sequences, with the exception of Gly-Pro-Arg, which corresponds to the $P_1'$-$P_2'$-$P_3'$ sequence of the cleavage site for thrombin of the alpha chain of fibrinogen, can be used in the context of the present invention.

For example, for the production of a chimeric protein in accordance with the invention, derived from PC, the $P_1'$-$P_2'$-$P_3'$ sequence may be the sequence Leu-Ile-Asp, which corresponds to the native $P_1'$-$P_2'$-$P_3'$ sequence of PC. Similarly, for the production of a chimeric protein in accordance with the invention, derived from FX, the $P_1'$-$P_2'$-$P_3'$ sequence may be the sequence Ile-Val-Gly, which corresponds to the native $P_1'$-$P_2'$-$P_3'$ sequence of FX.

Advantageously, it is also possible to use a $P_1'$-$P_2'$-$P_3'$ sequence in which one or more of the $P_1'$, $P_2'$ or $P_3'$ residues are modified so as to further improve the rate of activation by thrombin. Various modifications which influence activation by thrombin are described, for example, in the publication by LE BONNIEC et al. (1996), cited above.

The residues $P_1'$ to $P_3'$ (16 to 18 by chymotrypsin numbering) constitute, in serine proteases, the amino-terminal end of the catalytic domain of the active enzyme resulting from cleavage.

They are well conserved in serine proteases: the consensus sequence is $Ile^{16}$-$Val^{17}$-$Gly^{18}$. In particular, the positions $P_1'$ and $P_2'$ are almost systematically occupied by hydrophobic residues with aliphatic side chains, which develop hydrophobic interactions which play an important role in the formation and stabilization of the catalytic site of the activated serine protease.

In the case of PCa, residue 16 ($P_1'$) is a leucine, residue 17 ($P_2'$) an isoleucine and residue 18 ($P_3'$) an aspartate. In the case of FX, residue 16 ($P_1'$) is an isoleucine, residue 17 ($P_2'$) a valine and residue 18 ($P_3'$) a glycine.

However, the optimum sequence for cleavage by thrombin at these residues is Ser-Phe-Arg (at position $P_1'$, $P_2'$ and $P_3'$, respectively), i.e. a sequence very distant both from the consensus sequence of serine proteases and from the particular sequence of PC or FX, in particular due to the presence of a hydrophilic residue (serine) at position $P_1'$.

Under these conditions, it appears to be probable that, in particular in the case of PC and FX, a gain in affinity for thrombin which increases the activation rate risked being obtained to the detriment of the stability of the catalytic domain, and therefore of the activity of PCa and of FXa.

However, the inventors constructed PC and FX derivatives which, in addition to carrying, the FpA sequence upstream of the activating cleavage site, were modified so as to introduce an alanine or a serine at position $P_1'$ of the cleavage site as a replacement for the leucine of PC or for the isoleucine of FX, and/or a phenylalanine at position $P_2'$ as a replacement for the isoleucine of PC or for the valine of FX, and/or a glycine at position $P_3'$ as a replacement for the aspartate of PC.

They thus noted that these mutations promote activating cleavage of PC and of FX by thrombin and that, in addition, the PCa and FXa derivatives which result therefrom conserve a catalytic activity which, although decreased, is compatible with normal physiological function; in addition, this decrease in the catalytic activity is compensated by an increase in the half-life (up to 10-fold) compared to those of the nonmutated homologues of PCa and of FXa. This increase in half-life is the result of a better resistance to serine protease inhibitors in the plasma, conferred by these mutations.

According to a preferred embodiment of a serine protease zymogen derivative, and in particular of a PC or FX derivative, in accordance with the invention, the native $P_1'$-$P_2'$-$P_3'$ sequence of said zymogen is also modified by replacing the amino acid at position $P_1'$ with an alanine or a serine.

Other advantageous modifications of the native $P_1'$-$P_2'$-$P_3'$ sequence include for instance:
  the substitution of the amino acid at position $P_2'$ by a phenylalanine;
  the substitution of the amino acid at position $P_3'$ by a glycine.

Particularly preferred derivatives are those in which the amino acid at position $P_1'$ is replaced with an alamine.

The subject of the present invention is also any serine protease derivative, and ill particular any PCa or FXa derivative, which can be obtained by thrombin cleavage of a zymogen derivative in accordance with the invention in which one or more of the residues $P_1'$, $P_2'$ or $P_3'$ of the cleavage site has been modified as indicated above.

The serine protease derivatives in accordance with the invention have the advantage of being more resistant to plasmic serpins than the corresponding native serine proteases, and therefore of having a longer half-life.

The implementation of the present invention thus makes it possible:
  to obtain thrombin cleavage of proteins which do not constitute natural substrates for this enzyme, or to accelerate cleavage of proteins which are naturally only slowly cleaved by thrombin; it is thus possible in particular to readily and relatively inexpensively obtain active proteins from zymogens, by simple cleavage with thrombin, which is an inexpensive enzyme easy to obtain;
  to obtain, in addition, when the modification, as indicated above, of one or more of the residues $P_1'$, $P_2'$ or $P_3'$ of the cleavage site is produced, serine protease derivatives which are resistant to inhibitors and therefore have a longer plasma half-life.

Thus, by way of example, in the case of PC, the implementation of the present invention makes it possible to obtain PC derivatives whose rate of activation by thrombin in the absence of thrombomodulin is very much greater than that of the PC derivatives of the prior art. In addition, it makes it possible to prepare activated PC from these derivatives, using thrombin, whereas an activator extracted from snake venom, which is very expensive, is conventionally used to prepare PCa from native PC. With regard to the PCa derivatives which can be obtained in accordance with the invention, their relatively low activity is compensated, firstly, by the rate of activation and, secondly, by their considerable resistance to plasma serpins. The result of this is a therapeutic effect which is better targeted and more readily controlled than that of PCa or of the PC derivatives of the prior art.

Also by way of example, the implementation of the present invention makes it possible to obtain thrombin-activatable FX derivatives. In addition, it makes it possible to prepare FXa from these derivatives, using thrombin, whereas an activator extracted from snake venom, which is very expensive, is conventionally used to prepare FXa from native FX. With regard to the FXa derivatives which can be obtained in accordance with the invention, their possible low activity is compensated, firstly, by their sensitivity to thrombin and, secondly, by their relative resistance to plasma serpins. The result of this is a notable potential therapeutic effect which has no equivalent in the prior art.

Optionally, it is possible to combine the modifications specific to the derivatives of the invention with other modifications which concern different domains of the protein chosen and which may make it possible to improve some of its properties. Thus, in the case of the PC or PCa derivatives of the present invention, it is possible, for example, if the desire is to obtain a PCa derivative having a slightly greater anticoagulant activity, to substitute the Asn residues at positions 313 and 329 (with reference to the mature form of PC), as described in U.S. Pat. No. 5,453,373. In the case of the FX or FXa derivatives of the present invention, if the desire is to obtain a better yield of mature γ-carboxylated protein, it is possible to replace the propeptide of native FX with that of prothrombin as described by CAMIRE et al. (Biochemistry, 39, 14322-14329, 2000).

A subject of the present invention is also nucleic acid molecules encoding chimeric proteins, and in particular PC or FX derivatives, or serine protease derivatives according to the invention.

These nucleic acid molecules can be obtained by conventional methods well known to those skilled in the art, in particular by site-directed mutagenesis of the gene encoding the native protein for which it is desired to enable or accelerate cleavage by thrombin.

The present invention also encompasses pairs of nucleotide primers which can be used for obtaining, by site-directed mutagenesis, nucleic acid molecules encoding PC derivatives in accordance with the invention, and in particular the following pairs of primers:

a pair of oligonucleotides defined by the sequences SEQ ID NOS: 5 and 6,
a pair of oligonucleotides defined by the sequences SEQ ID NOS: 7 and 8,
a pair of oligonucleotides defined by the sequences SEQ ID NOS: 9 and 10,
a pair of oligonucleotides defined by the sequences SEQ ID NOS: 11 and 12,
a pair of oligonucleotides defined by the sequences SEQ ID NOS: 13 and 14.

The present invention also encompasses pairs of nucleotide primers which can be used for obtaining, by site-directed mutagenesis, nucleic acid molecules encoding FX derivatives in accordance with the invention, and in particular the following pairs of primers:

a pair of oligonucleotides defined by the sequences SEQ ID NOS: 15 and 16,
a pair of oligonucleotides defined by the sequences SEQ ID NOS: 17 and 18,
a pair of oligonucleotides defined by the sequences SEQ ID NOS: 19 and 20,
a pair of oligonucleotides defined by the sequences SEQ ID NOS: 21 and 22.

The present invention also encompasses the expression cassettes in which a nucleic acid molecule of the invention is associated with suitable elements for controlling transcription (in particular promoter and, optionally, terminator) and, optionally translation, and also the recombinant vectors into which a nucleic acid molecule in accordance with the invention is inserted. These recombinant vectors may, for example, be cloning vectors, or expression vectors.

The invention also includes gene delivery systems comprising a nucleic acid molecule of the invention, which can be used in gene therapy in vivo or ex vivo. This includes for instance viral transfer vectors such as those derived from retrovirus, adenovirus, adeno-associated virus, lentivirus, which are conventionally used in gene therapy. This also includes gene delivery systems comprising a nucleic acid molecule of the invention and a non-viral gene delivery vehicle. Examples of non-viral gene delivery vehicles include liposomes and polymers such as polyethylenimines, cyclodextrins, histidine/lysine (HK) polymers, etc.

A subject of the present invention is also prokaryotic or eukaryotic host cells genetically transformed with at least one nucleic acid molecule according to the invention. Preferably, for expressing and producing the chimeric proteins, and in particular the PC or FX derivatives in accordance with the invention, eukaryotic cells, in particular mammalian cells, will be chosen.

The present invention also encompasses transgenic animals, in particular transgenic non-human mammals hosting at least a transgene comprising an expression cassette of the invention. Said transgenic animals can be used for producing chimeric proteins of the invention, as already described for instance by BRINK et al., (Theriologenology, 53, 139-148 2000).

The construction of expression vectors in accordance with the invention, the transformation of the host cells, and the production of transgenic animals can be carried out using conventional molecular biology techniques.

The chimeric proteins, and in particular the PC or FX derivatives, or the serine protease derivatives of the invention, can, for example, be obtained by culturing genetically transformed cells in accordance with the invention and recovering the derivative expressed by said cell, from the culture. They may then, if necessary, be purified by conventional procedures, known in themselves to those skilled in the art, for example by fractionated precipitation, in particular ammonium sulphate precipitation, electrophoresis, gel filtration, affinity chromatography, etc.

In particular, conventional methods for preparing and purifying recombinant proteins may be used for producing the proteins in accordance with the invention. For example, for producing the PC derivatives in accordance with the invention, methods such as those described in U.S. Pat. No. 4,992,373 or U.S. Pat. No. 4,981,952 may be used.

A subject of the present invention is also the use of chimeric proteins, or of the products of thrombin cleavage thereof, in accordance with the invention, and in particular of the PC, PCa, FX or FXa derivatives in accordance with the invention, or of the nucleic acid molecules encoding these derivatives, for producing medicinal products. Said medicinal products are also part of the invention. They include for instance:

pharmaceutical compositions comprising at least one chimeric protein, or the product of thrombin cleavage thereof, in accordance with the invention, and in particular at least one PC, PCa, FX or FXa derivative in accordance with the invention, combined with a suitable excipient pharmaceutical compositions comprising a nucleic acid molecule of the invention associated with a viral or non-viral gene delivery vehicle. These pharmaceutical compositions may advantageously be used in gene therapy in vivo or en vivo. The vectors conventionally used in gene therapy, such as viral vectors (for example a vector of adenovirus or retrovirus type), liposomes, etc., can be used for the production of medicinal products in accordance with the invention.

For example, medicinal products obtained from PC or PCa derivatives in accordance with the invention can be used in all the usual applications of PC or PCa, and in particular as antithrombotics, anti-inflammatory and anti-apoptotic agents, and profibrinolytics, in the context of the prevention or treatment of pathologies involving hypercoagulation. By way of example, mention will be made of venous or arterial thromboses, in particular thromboses affecting the large calibre vessels, myocardial infarction, thrombotic disease, pulmonary embolism, the prevention of coronary reocclusions after an angioplasty or a thrombolysis, and also the treatment or prevention of clotting abnormalities in patients suffering from genetic abnormalities affecting the PC gene or that of thrombomodulin.

Medicinal products obtained from FX or FXa derivatives in accordance with the invention can be used as procoagulants. By way of example, mention will be made of the prevention or treatment of clotting pathologies of the haemorrhagic type, in particular ensuing from a factor VIII, LX or XI deficiency. These may in particular be haemophilias A or B, which may or may not be complicated by the presence of inhibitors (neutralizing allo antibodies directed against the factor VIII or IX conventionally used for treatment); they may also be acquired haemophilias resulting from the appearance of auto antibodies associated with another pathology (autoimmune disease, cancer, lymphoproliferative syndrome, idiopathic disorder, etc.).

The present invention will be more clearly understood from the further description which follows, which refers to nonlimiting examples of preparation and of characterization of PC and FX derivatives in accordance with the invention.

BRIEF DESCRIPTION OF THE DRAWINGS

FIG. 1 The polypeptide sequence of the heavy chain and the light chain of the mature form of PC of SEQ ID NO:1.

FIG. 2 The polypeptide sequence of the heavy chain and the light chain of the mature form of FX of SEQ ID NO:2.

EXAMPLE 1

Figure 3:
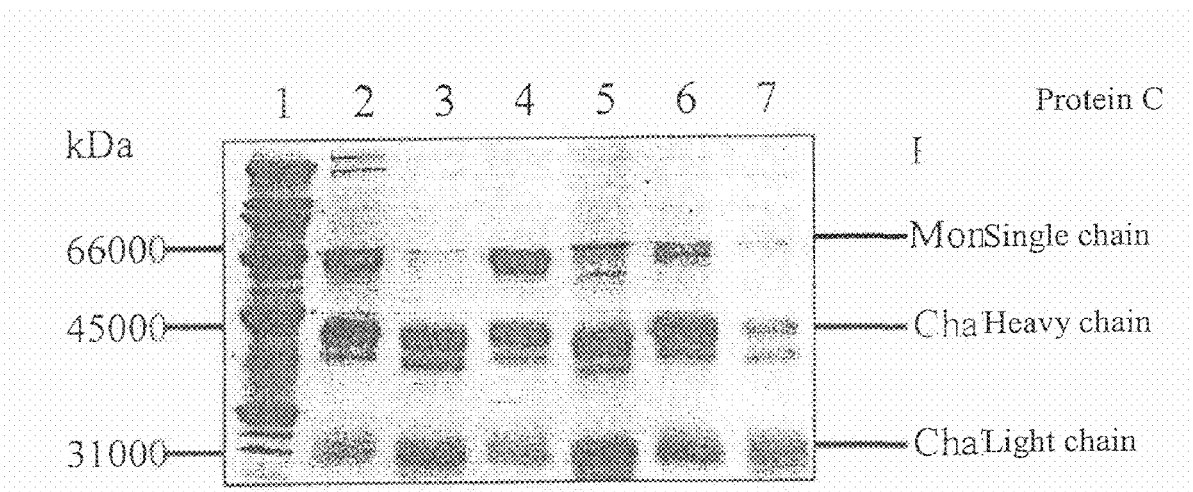
FIG. 3 Expression and purification of the PC variants. Lane 1: molecular mass markers. Lanes 2 to 7: 2 µg of variant Fpa-LID, $\Delta_{DTEDQED}$, Fpa-LFG, Fpa-SIG, Fpa-AIG and Fpa-LIG, respectively. The apparent molecular weight (in kDa) is indicated to the left of the gel. The position of the single-stranded form of normal PC, and also those of the heavy and light chains of normal PC are indicated to the right of the gel.

Construction of the Vectors for Expression of PC Variants

The vectors intended for expression of the PC variants were constructed using, as starting material, the vector pCI-neo-PC, which expresses normal human protein C after transfection into mammalian cells.

The PC cDNA was isolated from human liver cells by a reverse transcription polymerase chain reaction (PCR); the methods used to clone the cDNA into the vector pCI-Neo (PROMEGA, Madison, USA) are in accordance with those described in the literature (SAMBROOK et al., "Molecular cloning, A laboratory manual" (2nd edition), Cold Spring Harbor Laboratory Press, 1989; WHITE, PCR Protocols, Methods in Molecular Biology, Walker J. H. editors, Humana Press, Totowa, N.J., 1993).

Site-Directed Mutagenesis of the Vector pCI-neo-PC

The site-directed mutagenesis of the vector pCI-neo-PC, to prepare the vectors intended for expression of the PC analogues, was carried out using a method derived from that of JONES et al. (Nature, 344, 793-794, 1990). The modification of the PC cDNA making it possible to introduce the FpA sequence in place of the activation peptide, was obtained in a single PCR step, with the vector pCI-neo-PC as matrix and the pairs of oligonucleotides given in Table I as primers.

TABLE I

| Activation peptide sequence | $P_1'$-$P_3'$ sequence | Protein C | primer sequence | |
|---|---|---|---|---|
| DFLAEGGGVR (SEQ ID NO:2) | LID | Sense | 5'-GACTTTCTAgCTgAAggAggAggCgTgCggCTCATTgATgggAAgATgACC-3' | (SEQ ID NO: 3) |
| | | Antisense | 5'-CACgCTCCTCCTTCAgCTAgAAAgTCTCgTTTCAggTgACTgCgCTTCTT-3' | (SEQ ID NO: 4) |

TABLE I-continued

| Activation peptide sequence | $P_1'-P_3'$ sequence | Protein C primer sequence | | |
|---|---|---|---|---|
| DFLAEGGGVR (SEQ ID NO:2) | LFG | Sense<br>Antisense | 5'-GAAggAggAggCgTgCgCTCTTCggCgggAAgATgACCAggCg-3'<br>5'-CgCCTggTCATCTTCCCgCCgAAgAgCCgCACgCCTCCTTC-3' | (SEQ ID NO: 5)<br>(SEQ ID NO: 6) |
| DFLAEGGGVR (SEQ ID NO:2) | SIG | Sense<br>Antisense | 5'-gAAggAggAggCgTgCggTCCATTggCgggAAgATgACCAggCg-3'<br>5'-CgCCTggTCATCTTCCCgCCAATggACCgCACgCCTCCTCCTTC-3' | (SEQ ID NO: 7)<br>(SEQ ID NO: 8) |
| DFLAEGGGVR (SEQ ID NO:2) | AIG | Sense<br>Antisense | 5'-gAAggAggAggCgTgCgggCCATTggCgggAAgATgACCAggCg-3'<br>5'-CgCCTggTCATCTTCCCgCCAATggCCCgCACgCCTCCTCCTTC-3' | (SEQ ID NO: 9)<br>(SEQ ID NO: 10) |
| DFLAEGGGVR (SEQ ID NO:2) | LIG | Sense<br>Antisense | 5'-GAAggAggAggCgTgCggCTCATTggCgggAAgATgACCAggCg-3'<br>5'-CgCCTggTCATCTTCCCgCCAATgAgCCgCACgCTCCTCCTTC-3' | (SEQ ID NO: 11)<br>(SEQ ID NO: 12) |
| ΔDTEDQED (aa 1-7 of SEQ ID NO:24) | LID | Sense<br>Antisense | 5'-AgCgCAgTCACCTgAAACgACAAgTAgATCCgCggCTCAT-3'<br>5'-ATgAgCCgCggATCTACTTgTCgTTTCAggTgACTgCgCT-3' | (SEQ ID NO: 13)<br>(SEQ ID NO: 14) |

In this table, the first column indicates the modification introduced into the activation peptide: DFLAEGGGVR (SEQ ID NO:2) signifies that, in the derivative prepared, the activation peptide was replaced with the fibrino-peptide A sequence; $\Delta_{DTEDQED}$ signifies that, in the derivative prepared, the first 7 residues of the normal activation peptide were deleted. For each mutagenesis, the sequence of the pair of oligonucleotides used (sense and antisense) is given in the right-hand column. The central column of the table indicates the $P_1'$, $P_2'$ and $P_3'$ amino acid sequence of the activation site.

The PCR is carried out in a 50 µl volume containing 2.5 units of Pfu DNA polymerase (STRATAGENE; Amsterdam Zuidoost, the Netherlands), in the buffer recommended by the manufacturer, an equimolar mixture of each dNTP (0.5 MM), 125 ng of each primer (sense and antisense, see Table I) and 50 ng of matrix. The PCRs are carried out using a DNA Thermal Cycler type 480 (PERKIN ELMER, Roissy, France). Each reaction comprises an initial step of denaturation at 95° C. for 5 min, followed by 15 identical cycles which are each made up of three successive phases (denaturation, hybridization and elongation) of, respectively, 30 sec at 95° C., 60 sec at 55° C. or 60° C., and 20 min at 68° C.

To prepare the DFLAEGGGVR (SEQ ID NO:2) mutant having LID for residues $P_1'-P_3'$ (i.e. the natural residues), the primer hybridization temperature is 60° C.

The cDNA encoding this mutant is used to prepare the other variants in which the $P_1'-P_3'$ sequence differs from LID; the hybridization temperature being 55° C.

At the end of these 15 cycles, the vector which was used as the matrix is degraded at 37° C. for 60 min, with 10 units of DpnI restriction endonuclease (OZYME, Saint Quentin en Yvelines, France).

The preparation of the $\Delta_{DTEDQED}$ variant is carried out in the same way, with the vector pCI-neo-PC, containing the sequence encoding normal PC, as PCR matrix. The hybridization temperature is 55° C.

The variants in $P_1'-P_3'$ of the activation site of the PC derivative carrying FpA in place of the activation peptide were obtained in the same way, with the vector pCI-neo-PC-FpA (bearing the FpA sequence) as matrix and the corresponding pair of oligonucleotides, as indicated in Table I.

Preparation of Vectors Derived from pCI-neo-PC

Bacteria, strain DH5α (Dam+) are made competent by washing at 4° C. in 100 mM CaCl$_2$ and stored at −80° C. in a 100 mM CaCl$_2$ solution containing 15% of glycerol. An aliquot of competent bacteria (approximately 10$^6$ in 100 µl) is transformed with 5 to 10 µl of the PCR product digested with DpnI. The mixture is incubated for 30 mm at 4° C., and then subjected to a heat shock for 2 min at 42° C. followed by further incubation at 4° C. for 2 min. The bacteria are then incubated at 37° C. for 60 min in LB (LUTHIA BERTONI BROTH, INVITROGEN, Cergy Pontoise, France) medium with vigorous agitation. The LB medium is decanted after centrifugation at 2 000 rpm for 5 min, and the bacteria are plated out on agar (1.5% of AGAR-SELECT™ in LB medium containing 100 µg/ml of ampicillin). The Petri dishes are incubated in an incubator at 37° C. for 36 hours. 6 to 12 colonies are isolated and amplified overnight with vigorous agitation, at 37° C., in 5 ml of LB medium containing 100 µg/ml of ampicillin. The vector responsible for the ampicillin resistance is purified by the "boiling lysis" method (SAMBROOK et al., cited above). Alternatively, to prepare larger amounts of plasmid, the "PLASMID MIDY KIT" (QIAGEN, Courtaboeuf, France) was used according to the manufacturer's instructions.

Sequencing of the cDNAs of the PC Variants

The sequence of the cDNA carried by the derivatives of pCI-neo-PC was controlled using a method derived from that of SANGER et al. (Proc. Nati. Acad. Sci. USA, 74, 5463-5467, 1977), using an "ABI PRISM 377™" sequencer (PERKIN ELMER). The "ABI PRISM™ dRhodamine Terminator Cycle Sequencing Ready Reaction Kit" was used in accordance with the manufacturer's instructions. All of the cDNA of the PC derivatives was sequenced using 6 primers distributed along the PC cDNA sequence.

EXAMPLE 2

Transfection and Selection of Mammalian Cells Expressing a PC Variant

Transfection of HEK293 Cells

The transfected cell line is a human kidney epithelial cell line, HEK293 (CRL-1573), from the American Type Culture Collection. These cells were transfected with the vectors derived from pCI-neo-PC by the calcium phosphate coprecipitation method (SAMBROOK et al., cited above).

HEK293 cells are cultured in Petri dishes (80 mm diameter) at 37° C. in an atmosphere enriched with 5% $CO_2$, in complete medium: "Dulbecco's Modified Eagle Medium" (DMEM), supplemented with 10% of foetal calf serum, 2 mM of glutamate, 5 U/ml of penicillin and 5 μg/ml of streptomycin (all provided by INVITROGEN). When the cells reach 80% confluency, 5 to 40 μg of the vector to be transfected are diluted in 220 μl of $H_2O$ and added to 250 μl of 50 mM HEPES buffer, pH 7.05, containing 280 mM of NaCl, 10 mM of KCl, 1.5 mM of $Na_2HPO_4$ and 12 mM of dextrose (HBS, Hepes Buffered Saline). Coprecipitation of the DNA is obtained by adding, dropwise and with slow stirring, 31 μl of 2.5 M $CaCl_2$, followed by incubation for 30 min at ambient temperature. The cells are rinsed twice in phosphate buffer (PBS, INVITROGEN), and then returned to fresh complete medium. The DNA precipitate is then added and brought into contact with the HEK293 cells for 4 hours at 37° C. At the end of this incubation, the cells are washed with PBS and returned to culture in fresh complete medium for 24 h. The cells are then detached from the Petri dish by incubation for 5 min at 37° C. in the presence of 1.5 ml of a solution of trypsin-EDTA (INVITROGEN). The cells are then distributed into three Petri dishes and selected in complete medium containing 1 mg/ml of geneticin (INVITROGEN). The culture medium is renewed every 2 days for 2 to 3 weeks, until colonies are obtained. About 20 colonies are isolated, transferred into the wells (2 $cm^2$) of a 24-well culture plate, and returned to culture until confluency, in complete medium containing the selection agent. Each supernatant is then assayed by ELISA (see below) in order to detect the presence of PC derivatives. The clones which show the best expression of the PC derivative are amplified and made secure by freezing in liquid nitrogen (each vial containing approximately $10^6$ cells in 1 ml of calf serum mixed with 10% (v/v) of DMSO).

Identification of Clones Expressing a PC Variant

Identification of the clones expressing a PC derivative and estimation of the amount secreted were carried out by ELISA. A monoclonal antibody, P7058, described by MILETICH and BROZE (J. Biol. Chem., 265, 11397-11404, 1990) and marketed by SIGMA ALDRICH (St Quentin Fallavier, France), is used. This antibody is diluted in 50 mM $Na_2HCO_3$ buffer, pH 9.6, and adsorbed overnight at 4° C. (1 μg in 100 μl per well) onto a "MAXISORP™" titration plate (NUNC, POLYLABO, Strasbourg, France). The wells are washed 3 times in TTBS (50 mM Tris, pH 7.5, containing 150 mM NaCl and 0.5% (v/v) TWEEN 20™), and then saturated for 1 hour at ambient temperature with bovine serum albumin in TTBS (5% (w/v); 100 μl per well). An aliquot of each supernatant to be tested (100 μl diluted to 1/5 in DMEM medium containing 5 mM EDTA) is added to one of the wells of the saturated microtitration plate and left to incubate for one hour at ambient temperature. The wells are washed 3 times in TTBS, and an antibody directed against PC, prepared in a rabbit and coupled to peroxidase (DAKO, Glostrup, Denmark), is added after dilution to 1/1 000 in TTBS (100 μl per well). After incubation for one hour at ambient temperature, the wells are again washed 3 times in TTBS buffer. The presence of PC bound to the first antibody is revealed via the peroxidase activity borne by the second antibody by adding 100 μl of a solution of OPD (0.1 M citric acid, 0.1 M $Na_2HPO_4$, pH 5.0, containing 0.5% of $H_2O_2$ (v/v) and 1 mg/ml of orthophenylenediamine). After 5 to 15 mm, the reaction is stopped by adding 100 μl of 0.15 M $H_2SO_4$, and the product of the peroxidase-catalysed reaction is quantified by measuring absorbance at 490 nm.

EXAMPLE 3

Expression and Purification of the PC Variants

The transfected HEK293 cells are cultured in monolayer, in an incubator at 37° C. under a controlled atmosphere containing 5% $CO_2$, in complete medium. The clones derived from transfected HEK293 cells and which secrete a PC variant are amplified by successive passages in flasks of increasing surface area (tip to 300 $cm^2$). Each 300 $cm^2$ flask is then used to inoculate two roller bottles with a surface area of 850 $cm^2$. The supernatants, harvested after 2 to 6 days (depending on cell density) are centrifuged for 10 min at 5 000 rpm to remove the cell debris. The proteases possibly present in the culture medium are inhibited by adding 5 mM of EDTA and 10 mM of benzamidine, and the medium is stored at −20° C. before purifying the recombinant protein.

The PC variants are purified from the culture supernatants by three chromatography steps. Two liters of culture supernatant are first of all concentrated by adsorption on an anion exchange resin. These 2 liters of culture supernatant are diluted beforehand in 4 liters of 50 mM Tris buffer, pH 7.5, containing 5 mM of EDTA and 10 mM of benzamidine, in order to decrease the ionic strength; 4.5 g of SEPHADEX QAE A50™ (AMERSHAM PHARMACIA BIOTECH, Upsala, Sweden) are then added, and the mixture is stirred slowly for 1 hour at ambient temperature. After sedimentation of the SEPHADEX beads in a chromatography column, the proteins retained (including the PC) are eluted with 0.5 M NaCl in 50 mM Tris buffer, pH 7.5, containing 5 mM of EDTA and 10 mM of benzamidine. The PC is then purified by immuno-affinity chromatography using resins onto which the monoclonal antibodies (mab2) or HPC4 (ROCHE DIAGNOSTIC, Meylan, France) which recognize the EDQVDPRLIDGK sequence of the activation peptide have been grafted. These monoclonal antibodies were coupled to CNBr-activated SEPHAROSE 4B™ (approximately 1 mg of antibody per ml of gel), according to the supplier's (AMERSHAM PHARMACIA BIOTECH) recommendations. The normal recombinant PC and its analogue in which the activation peptide is truncated were purified using the resin coupled to the antibody HPC4.

The affinity column was loaded with the eluate from the QAE resin after having brought the Ca2+ concentration to 5 mM. The column was then washed in 50 mM Tris buffer, pH 7.5, containing 0.5 M of NaCl and 5 mM of Ca2+. The recombinant PC is eluted with a 50 mM Tris buffer, pH 7.5, containing 0.15 M of NaCl and 5 mM of EDTA.

The PC analogues in which the $P_3$-$P_3$' sequence is no longer DPRLID were purified using the resin coupled to the antibody mab2. In this case, after loading the affinity column with the eluate from the QAE resin, and washing in 50 mM Tris buffer, pH 7.5, containing 0.5 M of NaCl and 5 mM of EDTA, the recombinant PC is eluted by acidification in 0.1 M glycine buffer, pH 2.7. The pH of the eluted fraction is immediately corrected to 7.5 by adding 2 M Tris, pH 10. The final purification step is a further ion exchange chromatography, the aim of which is to reconcentrate and dialyse the eluate from the affinity chromatography. This eluate is diluted to 1/3 in a 50 mM Tris buffer, pH 7.5, containing 50 mM NaCl, and then adsorbed onto a FAST™ Q gel (AMERSHAM PHARMACIA BIOTECH). After washing in dilution buffer (10 times the column volume) to remove all traces of glycine and EDTA, the PC is eluted with 0.5 M NaCl in 50 mM Tris buffer, pH 7.5. The PC concentration is estimated from its absorbance at 280 nm, using a molar absorption coefficient ($E^{0.1\%}$) of 1.45. The purity of each PC analogue is evaluated on polyacrylamide gel (12% containing 0.1% of SDS) after denaturation and reduction of disulphide bridges by incubation in the presence of 5% of β-mercaptoethanol. The results of this analysis are illustrated in FIG. 3.

Legend of FIG. 3:

Lane 1: molecular mass markers. Lanes 2 to 7: 2 μg of variant Fpa-LID, $\Delta_{DTEDQED}$, Fpa-LFG, Fpa-SIG, Fpa-AIG and Fpa-LIG, respectively. The apparent molecular weight (in kDa) is indicated to the left of the gel. The position of the single-stranded form of normal PC, and also those of the heavy and light chains of normal PC are indicated to the right of the gel.

All the PC preparations obtained appear to be pure by SDS gel, but two forms are present. A double-stranded form is the major component (70 to 90%) with apparent molecular masses compatible with those expected for the heavy and light chains (41 000 and 21 000 Da, respectively). The remaining 10 to 30% are obtained in single-stranded form with an apparent molecular mass of 62 000 Da. The percentage of single-stranded form does not appear to depend on the analogue considered, but rather on the pool of culture supernatant from which the preparation is derived, independently of the nature of the mutation.

It should be noted, however, that, at the end of this purification protocol, part of the PC preparation is obtained in activated form (up to 50%). Since the activated form cannot be distinguished from the zymogen by SDS-polyacrylamide gel analysis, this percentage is evaluated by the amidolytic activity of the preparation (see below). The percentage of activated form appears to depend on both the PC analogue considered and the preparation batch considered. It is particularly high for the PC analogues which have a serine or an alamine in place of the normal leucine at position $P_1'$ of the activation site.

Neutralization of the Active Forms Present in the Preparations of PC Variants

In order to accurately measure the rate of activation by thrombin of each PC variant, it is essential to neutralize, beforehand, all traces of PCa possibly present in the preparation. This neutralization is carried out by irreversible inhibition of the active site of PCa. The covalent inhibitor used is D-Phe-Pro-Arg-$CH_3Cl$ (PPACK, CALBIOCHEM, St Cloud, France), which binds to $His^{57}$ of the charge stabilization system. In practice, 5 mM of PPACK are added to the PC preparation and the mixture is incubated for one hour at ambient temperature. This incubation is repeated twice, adding the same amount of PPACK (fresh). The PPACK which has not reacted is then removed by ion exchange chromatography. The PC and the inhibited PCa (but not the free PPACK) are adsorbed onto a RESSOURCE ™ Q column (AMERSHAM PHARMACIA BIOTECH) after dilution (1/10, v/v) in 50 mM Tris buffer, pH 7.5, containing 50 mM of NaCl. Before elution with 1 M NaCl in 50 mM Tris buffer, pH 7.5, the column is washed with 20 times its volume of dilution buffer. After treatment, the percentage of active form is less than 0.1% for most of the PC preparations, and does not exceed 0.4% for the PC analogue in which the residue at position $P_1'$ is a serine. The presence of neutralized PCa does not interfere with the thrombin activation of the zymogen fraction.

EXAMPLE 4

Characterization of the PC Variants

Determination of the Activation Rate

The rate constants for thrombin activation of the PC variants were determined under pseudo-first order conditions. In practice, the PC (1 μM) is incubated in the presence of thrombin (10 to 50 nM, depending on the PC variant) in kinetics buffer (50 mM Tris, pH 7.5, containing 0.15 M NaCl, 0.2% PEG 8000 (w/v), 0.5 mg/ml of bovine serum albumin and 5 nm $CaCl_2$). After varying incubation times, hirudin (200 units/ml) is added to a 5 μl aliquot of the reaction mixture (in order to stop the reaction and neutralize the thrombin).

The amount of PCa generated is then estimated by measuring the initial rate of hydrolysis of 200 μM of pyroGlu-Pro-Arg-pNA (S2366, BIOGENIC, Lattes, France). Variation in absorbance at 405 nm is recorded as a function of time using a microplate reader MR5000 (DYNEX, Guyancourt, France), and the PCa concentration is deduced by reference to a standard curve.

The rate constant for the reaction is then estimated by non-linear regression of the variation of PCa concentration as a function of time using an equation representing a first-order exponential increase: $PCa_{(t)}=PC(1-\exp^{(-k\ t)})+Cte$; in which $PCa_{(t)}$ represents the concentration of PCa at time t; PC represents the total concentration of (activatable) PC, and k represents the first-order rate constant; Cte is a constant which is added to take into account a possible (small) amidolytic activity present at the start, before addition of the activator (background noise). The values of $k_{on}$ (specificity constant) are calculated by forming the ratio of k to the concentration of activator (thrombin). The values obtained (in $M^{-1}\ s^{-1}$) are summarized in Table II.

TABLE II

|  | $k_{on}$ ($M^{-1} \cdot s^{-1}$) |
| --- | --- |
| PC | $3.0\ 10^2$ |
| PC (+TM) | $5.0\ 10^5$ |
| QVDPRLID | $6.0\ 10^2$ |
| (aa 165-172 of SEQ ID NO: 1) | |
| Fpa-LID | $1.1\ 10^4$ |
| Fpa-LIG | $1.6\ 10^4$ |
| Fpa-LFG | $2.9\ 10^4$ |
| Fpa-AIG | $3.0\ 10^4$ |
| Fpa-SIG | $1.6\ 10^5$ |

Substitution of the activation peptide of PC with fibrinopeptide A (variant Fpa-LID) increases the value of $k_{on}$ 40-fold. Further substitution in this variant of the aspartate $P_3'$ with a glycine (Fpa-LIG) only slightly increases $k_{on}$, but if the isoleucine at $P_2'$ is, in addition, substituted with a phenylalanine (Fpa-LFG), the value of $k_{on}$ becomes 96 times greater than that of normal PC. Finally, when the leucine at $P_1'$ is replaced with an alanine (Fpa-AIG) or with a serine (Fpa-SIG), the value of $k_{on}$ becomes, respectively, 100 and 500 times greater than that of normal PC, a value which is not that far from that of the activation of normal PC in the presence of thrombomodulin (PC+TM).

Preparative Activation of the PC Variants

For the functional studies, the PC and its derivatives were activated in preparative amounts with an activator isolated from the snake venom from *Agkistrodon cornortrix contor-* wix (PROTAC, KORDIA LEIDEN, the Netherlands). 9 units of PROTAC are coupled to 1 ml of activated SEPHAROSE-NHS™ (HI-TRAP, AMERSHAM PHARMACIA BIOTECH), respecting the manufacturer's recommendations.

An aliquot of 1 ml of PC (1 μM) in activation buffer (50 mM Tris, pH 7.5, containing 50 mM NaCl, 5 mM EDTA and 0.2% (w/v) PEG) is injected into the column grafted with PROTAC and equilibrated in the same buffer. The column is closed at both ends and the incubation is sustained for 8 hours at ambient temperature. The activated PC is eluted from the column by injecting 2 volumes of activation buffer.

Alternatively, in particular for the PC derivatives which can be rapidly activated by thrombin, the activation is carried out on a SEPHAROSE column grafted with purified human thrombin (1 mg/ml of gel). The gel is prepared and used under the same conditions as those described above for the column grafted with PROTAC™. The PCas are then reconcentrated by ion exchange chromatography on a MONO™ Q column (AMERSHAM PHARMACIA BIOTECH). The eluate from the HITRAP™ column is diluted (1/10; v/v) in 50 mM Tris, pH 7.5, and loaded onto the MONO™ Q column, and the PCa is eluted with 0.5 M NaCl in 50 mM Tris, pH 7.5.

Titration of the PCa Variants

The active site concentration of the activated PCa derivatives is determined by titration with PPACK™, which forms a covalent equimolar complex with the PCa.

Varying concentrations of PPACK™, of between 1 nM and 25 μM, are incubated with a fixed amount of the PCa to be titrated in kinetic buffer. The mixture is incubated at ambient temperature until completion of the reaction. The incubation time required depends on the PCa derivative considered and it is necessary to be sure that prolonging the incubation does not lead to the inhibition of additional PCa molecules: three hours of incubation are sufficient for normal PCa, but 18 hours are preferable for the PCa derivatives which have a serine or an alanine at position 16 and also for the derivative which has a phenylalanine at position 17.

At the end of this incubation, the residual concentration of the PCa is estimated by measuring the initial rate of hydrolysis of 200 μM of S2366. The variation in absorbance at 405 nm as a function of time ($v_s$) is recorded using an MR5000 microplate reader. The effective concentration of PCa initially present ($E_t$) is then estimated by non-linear regression of the dependency of $v_s$ as a function of the concentration of PPACK added, using the "tight-binding inhibition" equation (CHA, Biochem. Pharmacol., 24, 2177-2185, 1975; WILLIAMS and MORRISON, Methods Enzymol., 63, 437-467, 1979):

$$v_s = (v_0/2[E_t])\{[(K_i + [PPACK] - [E_t])^2 + 4K_i[E_t]]^{1/2} - (K_i + [PPACK] - E_t)\}$$

in which $v_0$ is the initial rate of hydrolysis of the S2366 in the absence of inhibitor, and $K_i$ is an apparent inhibition constant for the enzyme-inhibitor complex.

Amidolytic Activity of the PCa Variants

In order to characterize the active site of the PCa variants, the constants $K_{cat}$ and $K_M$ were determined for the hydrolysis of two chromogenic substrates: S2366 and D-Phe-Pip-Arg-pNA (S2238, BIOGENIC). The hydrolyses are carried out in kinetics buffer containing either 5 mM $CaCl_2$ or 5 mM EDTA, at ambient temperature. Varied concentrations of substrate, of between 50 and 3 000 μM, are incubated with a fixed amount of PCa (10 nM to 50 mM depending on the variant). The variation in absorbance at 405 nm as a function of time is recorded using an MR5000 microplate reader, and the initial rate of hydrolysis is estimated by linear regression of the absorbances corresponding at most to 10% hydrolysis. The constants $k_{cat}$ and $K_M$ are then estimated by non-linear regression of the variation of this initial rate as a function of the concentration of substrate, using the Michaelis-Menten equation.

The results obtained are summarized in Table III.

TABLE III

| | $k_{cat} s^{-1}$ | $K_M \mu M$ | $K_{cat}/K_M (\mu M^{-1} \cdot s^{-1})$ |
|---|---|---|---|
| | S2238 $Ca^{2+}$ | | |
| PCa | 28 | 440 | 63 |
| Fpa-LIG (activated) | 20 | 300 | 66 |
| Fpa-LFG (activated) | nd | nd | nd |
| Fpa-AIG (activated) | 10.8 | 747 | 14.5 |
| Fpa-SIG (activated) | 4.6 | 2030 | 2.3 |
| | S2238 EDTA | | |
| PCa | 20 | 530 | 37 |
| Fpa-LIG (activated) | 19 | 530 | 35 |
| Fpa-LFG (activated) | nd | nd | nd |
| Fpa-AIG (activated) | nd | nd | nd |
| Fpa-SIG (activated) | 0.49 | 275 | 1.8 |
| | S2366 $Ca^{2+}$ | | |
| PCa | 42 | 380 | 108 |
| Fpa-LIG (activated) | 46 | 575 | 80 |
| Fpa-LFG (activated) | 25 | >3000 | <8.3 |
| Fpa-AIG (activated) | 53 | 2600 | 20 |
| Fpa-SIG (activated) | 13 | >3000 | <4.3 |
| | S2366 EDTA | | |
| PCa | 37 | 400 | 92 |
| Fpa-LIG (activated) | 36 | 490 | 73 |
| Fpa-LFG (activated) | 21 | >3000 | <7 |
| Fpa-AIG (activated) | 20 | 1690 | 12 |
| Fpa-SIG (activated) | 2.2 | 2000 | 1.1 |

The active forms of the PC derivatives in which the residue at $P_1'$ is an alanine (Fpa-AIG) or a serine (Fpa-SIG), and also the derivative which carries a phenylalanine at $P_2'$ (Fpa-LFG), show a decrease in their amidolytic activity. ND: not determined. For the Substrate S2366, in the presence of Ca2+ mutation of the isoleucine to phenylalamine at position P2' causes a more than 8-fold increase in the $K_M$ and a 1.7-fold decrease in the $k_{cat}$. Substitution of the leucine at position $P_1'$ with an alamine or a serine leads to a 7-fold and 8-fold increase in the $K_M$, respectively. The $k_{cat}$ is decreased 3-fold with the variant carrying a serine at $P_1'$, whereas, for the variant carrying an alanine, the $k_{cat}$ is comparable to that determined with PCa. The $Ca^{2+}$-dependency of PCa with regard to the hydrolysis of these 2 substrates is conserved with the various PC variants: in the presence of EDTA, the $k_{cat}/K_M$ is slightly decreased.

The activated form of variant Fpa-SIG is that for which the specificity constant for hydrolysis of the substrates S2238 and S2366 is the most decreased.

Determination of the Plasma Half-Life of the PCa Variants

The half-life of the PCa variants was compared with that of normal PCa (recombinant PCa prepared under the same conditions or PCa purified from human plasma).

To estimate this half-life, the residual activity of the various PCas is measured after incubation for a varied period of time in normal plasma made unclottable by adding hirudin. The reaction mixture is composed, at 80% (v/v), of a pool of citrated normal plasmas and of PCa (50 to 200 mM depending on the variant) in 50 mM Tris buffer, pH 7.5, containing 150 mM of NaCl, 0.5 mg/ml of bovine serum albumin and 80 U/ml of hirudin. After incubation, an aliquot of the plasma/PCa/hirudin mixture (40 μl) is added to 160 μl of 250 μM S2366, and the initial rate of hydrolysis of the substrate is measured by recording, the increase in absorbance at 405 nm on an MR5000 microplate reader.

The half-life of each variant is then estimated by non-linear regression of the variation in residual activity as a function of time using an equation representing a first-order exponential decrease:

$$A_{(t)} = A_0 \exp^{(-k \cdot t)} + Cte;$$

in which $A_{(t)}$ represents the residual activity of the PCa at time t, $A_0$ represents its initial activity, and k represents the first-order rate constant. The constant Cte is added to take into account a possible activity independent of that of the PCa variant (background noise).

The plasma half-life is then calculated by dividing ln(2) by k.

The values obtained (in $min^{-1}$) are summarized in Table IV.

TABLE IV

|  | Half-life (min$^{-1}$) |
|---|---|
| PCa | 26 |
| Fpa-LIG (activated) | 56 |
| Fpa-LFG (activated) | 184 |
| Fpa-AIG (activated) | 147 |
| Fpa-SIG (activated) | 270 |

The half-lives were determined in citrated plasma by measuring the decrease in PCa activity as a function of time. The half-life is 10 times longer for the PCa variant in which the residue at $P_1'$ is a serine and the residue at $P_3'$ a glycine (Fpa-SIG).

The plasma half-life of the activated form of the variant Fpa-SIG is increased 10-fold compared to normal PCa.

Clotting Tests

The anticoagilant activities of PCa and of its derivatives were determined by measuring the prolongation of cephalin time with activator of a pool of recalcified citrated normal plasma, in the presence of varying concentrations of PCa or of one of its derivatives (RICHARSON et al., Nature, 360, 261-264, 1992).

These tests are carried out in duplicate on an ST4 machine (DIAGNOSTICA STAGO, Asnières, France). The activated forms of the PCas are diluted in a 50 mM Tris buffer, pH 7.5, containing 0.15 M NaCl and 0.5 mg/ml of bovine serum albumin. For each test, 50 µl of a dilution of PCa, 50 µl of the "APTT" reagent (ORGANON TECHNIKA, Fresnes, France) and 50 µl of the pool of citrated plasma are mixed and incubated for 3 min at 37° C. The clotting is triggered by adding 50 µl of dilution buffer containing 25 nM of $CaCl_2$.

Table V represents the anticoagulant activity of the PCa derivatives, expressed as percentage of the anticoagulant activity of 1 nM of normal PCa.

TABLE V

|  | Anticoagulant activity (%) |
|---|---|
| PCa | 100 |
| Fpa-LIG (activated) | 50 |
| Fpa-LFG (activated) | 8 |
| Fpa-AIG (activated) | 20 |
| Fpa-SIG (activated) | 6 |

The percentage of the anticoagulant activity is expressed relative to normal PCa, which serves as a reference (100% corresponds to the anticoagulant activity of 1 nM of PCa). For each variant, the concentration required to obtain an anticoagilant activity equivalent to 1 nM of PCa was estimated. The anticoagulant activity of the variant Fpa-AIG is, for example, 20% of that of normal PCa (5 nM of the variant are required to obtain the same activity as 1 nM of normal PCa).

The anticoagulant activity of the variant Fpa-SIG represents 6% of that of normal PCa.

Analysis of the Formation of Complexes of the Active Variants Fpa-AIG and Fpa-SIG with $\alpha_1$-antitrypsin The ability of the active forms of the variants Fpa-AIG and Fpa-SIG to form a stable complex with $\alpha_1$-antitrypsin (CALBIOCHEM) was demonstrated by incubating the activated PC variants (5 µM) with 40 µM of $\alpha_1$-antitrypsin, in kinetics buffer, for 5 h at 37° C.

The reaction product was analysed on 10% polyacrylamide gel under denaturing conditions. The results are given in FIG. 4.

Figure 4:
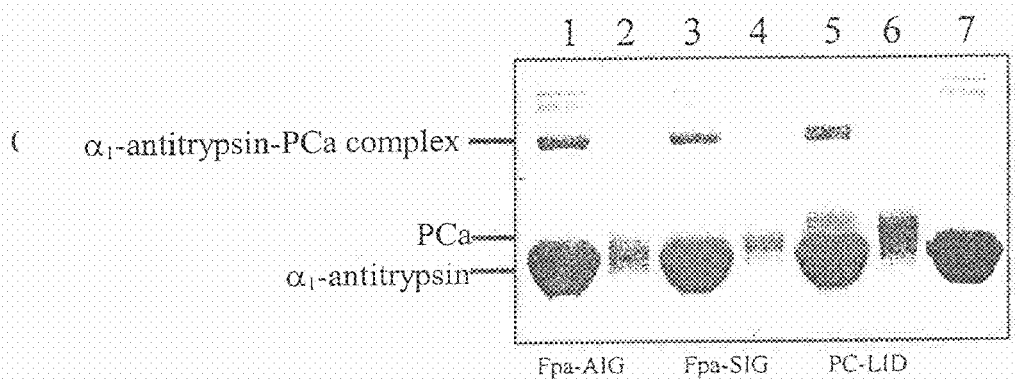
FIG. 4 A reaction product of the active forms of the variants Fpa-AIG and Fpa-SIG and $\alpha_1$-antitrypsin analyzed by 1% polyacrylamide gel under denaturing conditions. Lane 1: Fpa-AIG incubated for 5 hours at 37° C. in the presence of α1-antitrypsin, lane 2: Fpa-AIG alone (2 µg). Lane 3: Fpa-SIG incubated in the presence of α1-antitrypsin, lane 4: Fpa-SIG alone. Lane 5: normal PCa incubated in the presence of α1-antitrypsin, lane 6: normal PCa alone. Lane 7: α1-antitrypsin alone. All the PCa variants form a covalent complex with α1-antitrypsin.

Legend of FIG. 4:

Lane 1: Fpa-AIG incubated for 5 hours at 37° C. in the presence of α1-antitrypsin, lane 2: Fpa-AIG alone (2 µg). Lane 3: Fpa-SIG incubated in the presence of α1-antitrypsin, lane 4: Fpa-SIG alone. Lane 5: normal PCa incubated in the presence of α1-antitrypsin, lane 6: normal PCa alone. Lane 7: α1-antitrypsin alone. All the PCa variants form a covalent complex with α1-antitrypsin.

The formation of the stable complex between PCa and $\alpha_1$-antitrypsin results in the formation of a high molecular weight band. This gel reveals that the PCa variants in which the catalytic domain has an alanine or a serine at position 16 are capable of forming a stable complex with $\alpha_1$-antitrypsin at the normal physiological concentration of the serpin.

CONCLUSION

Effects of Modifying the Activation Peptide of PC

In the case of the PC derivative in which 7 of the 12 residues of the activation peptide (from $P_{12}$ to $P_6$, i.e. the sequence DTEDQED-amino acids 1-7 of SEQ ID NO:24) have been deleted, the activation rate (under physiological conditions and in the absence of thrombomodulin) is doubled compared to that of normal PC expressed and characterized under the same conditions. This shows that the activation peptide therefore limits the ability of thrombin to cleave PC: it is thought to constitute one of the barriers which limit its activation in the absence of thrombomoduline.

In the case of the PC derivative in which the 12 residues of the activation peptide (from $P_{12}$ to $P_1$, i.e. the sequence DTEDQEDQVDPR-SEQ ID NO:24) have been removed and replaced with the sequence of human FpA (from $P_{10}$ to $P_1$, i.e. the sequence DFLAEGGGVR-SEQ ID NO:2), the activation rate (under the physiological conditions and in the absence of thrombomodulin) is 40 times greater than that of normal PC expressed and characterized under the same conditions. Overall, modification of the activation peptide of PC made it possible to achieve an activation rate constant of $2 \times 10^4 M^{-1} s^{-1}$.

Optimization of the Residues $P_1'$, $P_2'$ and $P_3'$ of the Activation Site of PC The inventors expressed and characterized PC variants which, in addition to carrying the FpA sequence upstream of the activating cleavage site, were modified at positions 16, 17 and/or 18. At position 16, the leucine was replaced with a serine or an alanine; at position 17, the isoleucine was substituted with a phenylalanine, and at position 18, the aspartate was substituted with a glycine. All these mutations bring, to a lesser or greater degree, the activation site of PC closer to the optimal cleavage sequence of thrombin, and all of these effectively increase the susceptibility of each variant to the activator. The difference is particularly spectacular with the variant carrying a serine at 16 and a glycine at 18, since the value of the activation constant obtained ($1.6 \times 10^5$ $M^{-1}s^{-1}$) is of the same order of magnitude as that obtained for normal PC in the presence of thrombomodulin ($5 \times 10^5$ $M^{-1}$ $s^{-1}$; Table II).

The gain relative to the PC derivative carrying only FpA upstream of the cleavage site is, with this mutant, more than 10-fold. This gain comes especially from the L16S mutation, since the contribution of the D18G mutation is only 1.6-fold (Table II).

When residue 16 is an alanine, the gain is approximately 2-fold (relative to the mutant carrying FpA and mutated at D18G); this being a gain which is similar to that obtained when substituting the isoleucine at 17 with a phenylalanine.

However, except for the D18G mutation, these modifications have (to varying degrees) a deleterious consequence on the catalytic activity of the PCa. When residue 16 is at serine, the anticoagulant activity is 20 times lower than for normal PCa, when residue 16 is all alanine, the anticoagulant activity is 5 times lower, it is 13 times lower when residue 17 is a phenylalanine.

This (relative) loss of activity probably reflects an impairment of the catalytic machinery itself since the value of the specificity constant ($k_{cat}/K_M$) for a chromogenic substrate such as S2366 or S2238 is decreased, in similar proportions (27-fold when a serine is at position 16, 5-fold when it is an alanine, and 12-fold when residue 17 is a phenylalanine). It is conceivable that the serine, and to a lesser degree the alanine, do not make it possible to form all the contacts necessary for maximum activation of the catalytic machinery; the hydrophobicity of alanine being lower than the other aliphatic residues, valine, leucine or isoleucine, while the serine residue is hydrophilic in nature. Hydrophobicity is probably not, on the other hand, the cause of the loss of activity resulting from the mutation at position 17, since the hydrophobicity of a phenylalanine is comparable to that of a leucine. The destabilizing effect may result from steric hindrance, the side chain of a phenylalanine carrying a greater volume (190 $A^3$) than that of a leucine (124 $A^3$); alternatively, a repulsion may be produced between the charge of Asp$^{189}$ and that, partial, of the aromatic ring of the phenylalamine.

The catalytic deficiency of the activated mutants obviously rapidly poses the question of the overall effective gain subsequent to the mutation. At first glance, this gain is not favourable since the increase in activation rate appears to be entirely lost by the deficiency in activity: the ratio of the gain in activation rate to the loss of catalytic activity is less than one (10/20 and 2/5 for serine and alanine at position 16, 2/13 for a phenylalanine at position 17).

However, this deficiency in activity is accompanied by a relative resistance to plasma inhibitors and, consequently, prolongs their action. Thus, compared to normal PCa, the plasma half-life of the mutant carrying a serine at 16 is increased 10-fold, that of the mutant carrying an alanine is increased 5- to 6-fold, and that of the mutant carrying a phenylalanine at 17 is increased 7-fold. Under these conditions, while the overall effective gain remains less than 1 for the mutant with phenylalanine at 17, and remains close to zero for the L16S mutation, it becomes highly favourable for the mutant carrying an alanine at 16. Overall, despite a decreased catalytic activity, the activation rate and the increase in plasma half-life confer on the L16A mutant a considerable advantage over all the other PC derivatives described to date.

EXAMPLE 5

Construction of Vectors for Expression of FX Variants

The vectors intended for expression of the FX variants were constructed using, is starting material, the vector pNUT-FX, which expresses normal human FX after transfection into mammalian cells (BIANCHINI et al., J. Biol. Chem. 277, 20527-20534, 2002.

The Site-Directed Mutagenesis of the Vector pNUT-FX

The site-directed mutagenesis of the vector pNUT-FX in order to prepare the vectors intended for expression of the FX analogues was carried out by a method derived from that of JONES et al. (cited above). The modification of the FX cDNA for introducing the FpA sequence in place of the activation peptide was obtained in a single PCR step, with the vector pNUT-FX as matrix and the pairs of oligonucleotides given in Table VI as primers.

In native FX, the sequence of the residues $P_3$-$P_2$-$P_1$-$P_1$'-$P_2$'-$P_3$' bordering the cleavage site (cleavage taking place between $P_1$ and $P_1$') is LTR-IVG (SEQ ID NO:25). The four FX analogues prepared: FpA-IVG, FpA-IFG, FpA-AVG and FpA-AFG, have for sequence $P_3$-$P_2$-$P_1$-$P_1$'-$P_2$'-$P_3$': GVR-IVG (amino acids 8-12 of SEQ ID NO:26), GVR-IFG (amino acids 8-12 of SEQ ID NO:27), GVR-AVG (amino acids 8-12 of SEQ ID NO:28) and GVR-AFG (amino acids 8-12 of SEQ ID NO:29) respectively.

The vectors expressing these FX analogues were prepared by site-directed mutagenesis. The sequence of the primers used for this mutagenesis of the vector pNUT-FX is given in Table VI.

TABLE VI

| Activation peptide sequence | $P_1$'-$P_3$' sequence | Factor X | | primer sequence |
|---|---|---|---|---|
| DFLAEGGGVR (SEQ ID NO:2) | IVG | Sense | | 5'-gACTTTCTAgCTgAAggAggAggCgTgAggATCgTgggAggCCAggAATgC-3' (SEQ ID NO: 15) |
| | | Antisense | | 5'-CACgCCTCCTCCTTTCAgCTAgAAAgTCCCTCTTCCTgCgTTCCAgggTCTg-3' (SEQ ID NO: 16) |
| DFLAEGGGVR (SEQ ID NO:2) | IFG | Sense | | 5'-gACTTTCTAgCTgAAggAggAggCgTgAggATCTTCggAggCCAggAATgCAAgg-3' (SEQ ID NO: 17) |
| | | Antisense | | 5'-gAAgATCCTCACgCCTCCTCCTTCAgCTAgAAAgTCCCTCTTCCTgCgTTCCAgggTCTg-3' (SEQ ID NO: 18) |

TABLE VI-continued

| Activation peptide sequence | $P_1'-P_3'$ sequence | Factor X primer sequence | |
|---|---|---|---|
| DFLAEGGGVR (SEQ ID NO:2) | AVG | Sense | 5'-ggAggAggCgTgAgggCCgTgggAggCCAggAATg-3' (SEQ ID NO: 19) |
| | | Antisense | 5'-CATTCCTggCCTCCCACggCCCTCACgCCTCCTCC-3' (SEQ ID NO: 20) |
| DFLAEGGGVR (SEQ ID NO:2) | AFG | Sense | 5'-ggAggAggCgTgAgggCCTTCggAggCCAggAATgCAAg-3' (SEQ ID NO: 21) |
| | | Antisense | 5'-CTTgCATTCCTggCCTCCgAAggCCCTCACgCCTCCTCC-3' (SEQ ID NO: 22) |

In this table, the first column indicates the modification introduced into the activation peptide: DFLAEGGGVR (SEQ ID NO:2) signifies that, in the derivative prepared, the entire activation peptide of FX has been replaced with the fibrinopeptide A sequence. For each mutagenesis, the sequence of the pair of oligonucleotides used (sense and antisense) is given in the right-hand column. The central column of the table indicates the $P_1'$, $P_2'$ and $P_3'$ amino acid sequence of the activation site.

The PCR is carried out in a 50 μl volume containing 2.5 units of Pfu DNA polymerase (STRATAGENE; Amsterdam Zuidoost, the Netherlands) in the buffer recommended by the manufacturer, an equimolar mixture of each dNTP (0.5 mM), 125 ng of each primer (sense and antisense, see Table VI) and 50 ng of matrix. The matrix used to prepare the derivatives DFLAEGGGVR-IVG (SEQ ID NO:26) and DFLAE-GGGVR-IFG (SEQ ID NO:27) is pNUT-FX; the hybridization temperature is 55° C. The matrix used to prepare the derivatives DFLAEGGGVR-AVG (SEQ ID NO:28) and DFLAEGGGVR-AFG (SEQ ID NO:29) is pNUT-FX, DFLAEGGGVR-IVG (SEQ ID NO:26)-derived beforehand; the hybridization temperature is 50° C. The PCRs are carried out using a DNA Thermal Cycler type 480 (PERKIN ELMER). Each reaction comprises an initial step of denaturation at 95° C. for 5 min, followed by 16 identical cycles which are each made up of three phases (denaturation, hybridization and elongation) of, respectively, 45 sec at 95° C., 60 sec at 55° C. (or 50° C.) and 26 min at 68° C. At the end of these 16 cycles, the vector which has served as matrix is degraded at 37° C. for 1 hour with 10 units of DpnI (OZYME).

Preparation of Vectors Derived from pNUT-FX

Bacteria, strain DH5α (Dam+) are made competent by washing at 4° C. in 100 mM $CaCl_2$ and stored at −80° C. in a 100 mM $CaCl_2$ solution containing 15% of glycerol. An aliquot of competent bacteria (approximately $10^6$ in 100 μl) is transformed with 5 to 10 μl of the PCR product digested with DpnI. The mixture is incubated for 30 mm at 4° C., and then subjected to a heat shock for 2 mm at 42° C. followed by further incubation at 4° C. for 2 min. The bacteria are then incubated at 37° C. for 60 min in LB (LUTHIA BERTONI BROTH, INVITROGEN) medium with vigorous agitation. The LB medium is decanted after centrifugation at 2 000 rpm for 5 min, and the bacteria are plated out on agar (1.5% of AGAR-SELECT™ in LB medium containing 100 μg/ml of ampicillin). The Petri dishes are incubated in an incubator at 37° C. for 36 hours. 6 to 12 colonies are isolated and amplified overnight with vigorous agitation, at 370C, in 5 ml of LB medium containing 100 jag/ml of ampicillin. The vector responsible for the ampicillin resistance is purified by the "boiling lysis" method (SAMBROOK et al., cited above). Alternatively, to prepare larger amounts of plasmid, the "PLASMID MIDY KIT" (QIAGEN, Courtaboeuf, France) was used according to the manufacturer's instructions.

Sequencing of cDNAs of the FX Variants

The sequence of the cDNA carried by the derivatives of pNUT-FX was controlled by a method derived from that of SANGER et al. (cited above), using an "ABI PRISM 377™" sequencer (PERKIN ELMER). The "ABI PRISM™ dRhodamine Terminator Cycle Sequencing Ready Reaction Kit" was used in accordance with the manufacturer's instructions. The sequencing of the entire FX cDNA contained in the derivatives of pNUT-FX was carried out using a minimum of 6 primers distributed along the sequence of the FX cDNA.

EXAMPLE 6

Transfection and Selection of Mammalian Cells Expressing an FX Variant

Transfection of BHK-21 Cells

The recombinant proteins were expressed in newborn hamster kidney (BHK-21) cells provided by the European Collection of Cell Cultures (Sofia-antipolis, France). These cells were transfected with the vectors derived from pNUT-FX, by the calcium phosphate coprecipitation method (SAMBROOK et al., cited above.

The BHK-21 cells are cultured in Petri dishes (80 mm diameter) in an incubator at 37° C. under an atmosphere of 5% $CO_2$, in complete DMEM medium (Dulbecco's Modified Eagle 15 Medium; INVITROGEN): supplemented with 10% of foetal calf serum (INVITROGEN), 2 mM of L-glutamine (INVITROGEN), 100 units/ml of penicillin (INVITROGEN) and 100 μg/ml of streptomycin (INVITROGEN). When they reach approximately 80% confluency, the cells are rinsed twice in PBS buffer (INVITROGEN) and then incubated at 37° C. for 1 hour in 4 ml of OPTI-MEM™ (INVITROGEN).

The transfection is carried out by adding 40 nM of the vector pNUT-FX or one of its derivatives (40 μg in a volume of 220 μl adjusted with distilled water) to 250 μl of a solution, at a pH of exactly 7.05, composed of 50 mM HEPES, 1.5 mM $Na_2HPO_4$, 280 mM NaCl, 10 mM KCl and 12 mM dextrose. Coprecipitation of the DNA is obtained by adding 31 μl of 2.5 M CaCl, dropwise and with constant stirring. After 30 min of incubation at ambient temperature, the precipitate is added to the medium covering the cells and left to sediment for 3 hours at 37° C. The cells are washed with PBS (in order to remove most of the precipitate) and returned to culture in complete DMEM medium for 24 hours at 37° C. The cells are detached from the Petri dish with 2 ml of a solution of EDTA at 54 mM, pH 8.0, containing 0.5 mg/ml of trypsin, are resuspended in the selection medium (complete DMEM containing 50 mg/L of methotrexate (TEVA, Courbevoie, France), and are re-seeded in two new Petri dishes. The culture medium is renewed every two days for two to three weeks, until colonies are obtained, which are isolated and transferred into the wells (2 cm²) of a culture plate, where they are multiplied to confluency in the selection medium.

Identification of Clones Producing an FX Derivative

The clones stably expressing an FX derivative are detected by immunoblotting. An aliquot (30 µl) of BHK-21 cell culture supernatant, which remained in contact with the transfected cells for at least 48 hours, is added to 10 µl of 100 mM Tris, pH 6.8, containing 40% (v/v) of glycerol, 8% (w/v) of SDS, 0.04% (w/v) of bromophenol blue and 20% (v/v) of β-mercaptoethanol. The proteins in the sample are denatured at 95° C. for 5 min, and are separated on 12% polyacrylamide gel (crosslinking 29/1) in a 25 mM Tris buffer, pH 7.5, containing 0.1 M glycine and 0.1% (w/v) SDS.

The electrophoresis is followed by transfer onto a nitrocellulose membrane (TRANS-BLOT™, BIO-RAD, Ivry sur Seine, France) in 25 mM Tris buffer, 0.1 M glycine, pH 7.5, containing 20% of methanol. The membrane is saturated by incubation for 1 hour at ambient temperature in a solution of skimmed milk (5%, w/v) in 50 mM Tris buffer, pH 7.5, containing 150mM of NaCl and 0.1% of Tween 20 (TTBS), and then washed 3 times for 10 min in the same buffer. The membrane is then incubated for 1 to 12 hours in the presence of 50 ng/ml of the monoclonal antibody 9E10 (CLONTECH, Palo Alto, Calif., USA) in TTBS.

After three washes (as above), the membrane is incubated for one hour at ambient temperature in the presence of a goat anti-mouse IgG polyclonal antibody labelled with alkaline phosphatase (BIO-RAD), diluted to 1/3000 in TTBS. The presence of recombinant FX is revealed by incubating the membrane in the presence of a chromogenic substrate (mixture in equal amounts of 5-bromo-4-chloro-3-indolyl phosphate, toluidine salt (BCIPT) and nitrotetrazolium chloride (NTC), diluted in 0.1 M Tris buffer, pH 9.5, containing 0.5 M of $MgCl_2$).

EXAMPLE 7

Expression and Purification of FX Variants

Cell Culture and Production

The cells expressing the FX derivative are multiplied by successive passages in 150 cm² flasks which are used to inoculate 850 cm² bottles. The production is carried out at 37° C. under a controlled atmosphere containing 5% of $CO_2$, in selection medium containing 50 µM of $ZnCl_2$ (to induce the metallothionein promoter) and 5 µg/ml of vitamin K (ROCHE, Neuilly sur Seine, France) to allow post-translational γ-carboxylation. The culture supernatants are harvested every 2 to 6 days (depending on cell density), clarified by centrifugation for 10 min at 5 000 g, and stored at −20° C. after addition of 5 mM EDTA and 10 mM of benzamidine.

The FX derivatives are purified in three stages. The first is adsorption onto anion exchange resin in order to concentrate the proteins contained in the culture supernatant. The supernatants are diluted to 1/3 in 50 mM Tris, pH 7.5, containing 10 mM of benzamidine and 5 mM of EDTA. Typically, two liters of supernatant are diluted in four liters of buffer, 4.5 grams of QAE SEPHADEX A50™ (AMERSHAM PHARMACIA BIOTECH) are added, and the mixture is stirred slowly for 30 mm at ambient temperature (using a rotary paddle stirrer).

The SEPHADEX beads are left to sediment and the supernatant is discarded. The loaded resin is transferred into a column and the proteins adsorbed are eluted with 50 mM Tris buffer, pH 7.5, containing 0.5 M NaCl. The second stage is affinity chromatography to separate the FX derivative from the other proteins contained in the QAE- SEPHADEX™ eluate. The eluate is loaded onto an AFFI-PREP HZ gel (BIO-RAD) grafted (3 mg/ml of gel) with the monoclonal antibody 9E10 (CLONTECH). After washing in 50 mM Tris buffer, pH 7.5, containing 0.5 M of NaCl, the FX derivative is eluted in 0.1 M glycine-HCl buffer, pH 2.7. The pH of the eluate is adjusted to 7.5 by adding 30 µl/ml of 2 M Tris, and the column is re-equilibrated in the washing buffer. The final stage of the purification is further anion exchange chromatography to remove the glycine and concentrate the derivative eluted from the affinity column. Several eluates, totalling 1 to 10 mg of FX derivative, are pooled, diluted to 1/4 in 50 mM Tris buffer, pH 7.5, containing 5 mM EDTA, and loaded onto a Q-SEPHAROSE FAST FLOW™ column (0.8×10 cm) (AMERSHAM PHARMACIA BIOTECH). After washing in dilution buffer, the column is eluted with 50 mM Tris buffer, pH 7.5, containing 0.5 M NaCl.

A minimum of 1 mg of each FX derivative is prepared; the purity of each preparation is controlled, after denaturation and reduction of a sample, by polyacrylamide gel electrophoresis (12%, crosslinking 29/1) and staining with Coomassie blue. All the preparations obtained appear to be pure in SDS-polyacrylamide gel, but two forms are systematically present: a major double-stranded form (80 to 90%), with apparent molecular masses compatible with those expected for the heavy and light chains of the FX derivatives, and a minor single-stranded form (10 to 20% depending on the preparations), with a molecular mass of 46 kDa. The percentage of single-stranded form appears to depend rather on the pool of supernatants from which the preparation is derived than on the mutation introduced: for a given mutation, the percentage of single-stranded form varies from one purification to the other. The purified derivatives are aliquoted and stored at −80° C. until use. The concentration of the aliquot is estimated from its absorbance at 280 nm, talking 1.25 $g^{-1}$ $cm^{-1}$ as absorption coefficient (e %280).

EXAMPLE 8

Characterization of the FX Variants

Determination of the Rate of Activation by Thrombin

The rate constants for thrombin-activation of the FX variants were determined under pseudo-first order conditions. In practice, the FX derivative (1 or 2 µM) is incubated in the presence of thrombin (100 nM) in kinetics buffer (50 mM Tris, pH 7.8, containing 0.15 M NaCl, 0.2% PEG 8000 (w/v) and 5 mM $CaCl_2$), at 37° C. After varying incubation times, hirudin (100 units/ml) is added to a 5 µl aliquot of the reaction mixture (in order to stop the reaction by neutralizing the thrombin).

The proportion of FXa generated is then estimated by measuring the initial rate of hydrolysis of 100 µM of N-α-Z-Arg-Gly-Arg-pNA (S2765, BIOGENIC). The variation in absorbance at 405 nm is recorded as a function of time using an MR5000 microplate reader. The reaction is continued until an activation plateau is reached (when the rate of hydrolysis of S2765 no longer increases even with longer incubation of the FX derivative with thrombin).

The rate constant for the reaction is then estimated by non-linear regression of the variation in rate of hydrolysis of the S2765 as a function of time of incubation of the FX derivative with thrombin, using an equation representing a first-order exponential increase: $v_{(t)}=V_{max}(1-\exp^{(-k\ t)})+V_o$; in which $v_{(t)}$ represents the rate of hydrolysis of S2765 at time t; $V_{max}$ represents the maximum rate of hydrolysis (at the plateau) and k represents the first-order rate constant; $V_o$ is a constant which is added to take into account a possible (small) amidolytic activity present at the start, before addition of the activator (background noise). The values of $k_{on}$ (specificity constant) are calculated by forming the ratio of k to the concentration of activator (thrombin). The values obtained (in $M^{-1}\ s^{-1}$) are summarized in Table VII.

TABLE VII

| | $k_{on}\ (M^{-1}\cdot s^{-1})$ |
|---|---|
| FX | nd |
| FpA-IVG | $4.0\ 10^2$ |
| FpA-IFG | $3.0\ 10^3$ |
| FpA-AVG | $2.2\ 10^3$ |
| FpA-AFG | $2.4\ 10^5$ |

Substitution of the activation peptide of FX with fibrinopeptide A (variant FpA-IVG) therefore makes it possible to transform FX (the thrombin-activation of which is undetectable: ND) into a thrombin-sensitive zymogen ($k_{on}$ $4\times10^2\ M^{-1}\ s^{-1}$). The additional substitution in this variant of the valine at $P_2'$ with a phenylalanine (FpA-IFG) increases this rate 7.5-fold. If the isoleucine at $P_1'$ is substituted with an alanine (FpA-AVG), this rate increases 5.5-fold. Finally, when tile isoleucine at $P_1'$ is replaced with an alanine and the valine at $P_1'$ is replaced with a phenylalanine (FpA-AFG), the value of $k_{on}$ becomes 625 times greater than that of the FX derivative FpA-IVG. The catalytic activity of the activated derivatives obtained from FpA-AIG, FpA-IFG and especially FpA-AFG is greatly decreased relative to the activated derivative obtained from FpA-IVG. The derivative FpA-IVG should generate, after activation, an FXa identical in every way to normal FXa since the activation peptide is released during activation. The other derivatives generate FXas in which the residue $P_1'$ and/or $P_2'$ is modified, which disturbs the catalytic activity to a lesser or greater degree.

Preparative Activation of FX Variants

For the functional studies, the Fx and its derivatives were activated in preparative amounts. The FX (non-thrombin-activatable) was activated by passing it over a column of SEPHAROSE-NHS ™ (HITRAP, AMERSHAM PHARMACIA BIOTECH) grafted, at 5 mg/ml of gel, with the FX activator isolated from Russell viper venom (RVV-X, KORDIA, Leiden, the Netherlands) and prepared by respecting the manufacturer's recommendations. The thrombin-activatable FX derivatives were activated to FXa derivatives by passing them over a column of SEPHAROSE-NHS grafted, at 1 mg/ml of gel, with thrombin, also prepared by respecting the manufacturer's recommendations.

Four milligrams of FX derivative in kinetics buffer are introduced into the activation column. The column is closed at both ends and the incubation is sustained for 16 hours at ambient temperature. The activated derivative is eluted with 50 mM Tris, pH 7.5, containing 0.5 M NaCl and 5 mM $CaCl_2$. The eluate contains the activated form but, since the activation is not always complete, some nonactivated form possibly remains. To separate the activated form from the non-activated form, the eluate is diluted to 1/3 in 50 mM Tris, pH 7.5 containing 5 mM of $CaCl_2$ (to reduce the ionic strength), loaded onto a 1 ml heparin- SEPHAROSE HITRAP™ column (AMERSHAM PHARMACIA BIOTECH) and eluted with 50 mM Tris buffer, pH 7.5, containing 0.5 M NaCl and 5 mM of $CaCl_2$.

Titration of the Activated Form of the FX Variants

The active site concentration of the activated FX derivatives is determined by titration with D-Phe-Phe-Arg-$Ch_3Cl$ (FFRCK (SEQ ID NO:30); marketed by CALBIOCHEM), which forms an equimolar covalent complex with the FXa.

Varying concentrations of FFRCK (SEQ ID NO:30), of between 20 nM and 12 µM, are incubated with a fixed amount (0.5 to 1 µM) of FXa derivative to be titrated, in kinetics buffer. The mixture is incubated at ambient temperature until completion of the reaction. The incubation time required depends on the FXa derivative considered, and it is necessary to ensure that prolonging the incubation does not cause inhibition of additional FXa molecules: three hours of incubation are sufficient for normal FXa and the activated form of the derivative FpA-IVG, but 18 hours are not sufficient for the FXa derivatives which have an alanine at position 16 and/or a phenylalanine at position 17, and which are difficult to titrate by this method.

At the end of this incubation, the residual concentration of the FXa derivative is estimated by measuring the initial rate of hydrolysis of 100 µM S2765. The variation in absorbance at 405 nm as a function of time $(v_s)$ is recorded using an MR5000 microplate reader. The effective concentration of the FXa derivative initially present $(E_t)$ is then estimated by non-linear regression of the dependency of $v_s$ as a function of the concentration of FFRCK added, using the "tight-binding inhibition" equation (CHA; WILLIAMS and MORRISON, cited above):

$$v_s=(v_0/2[E_t])\{[K_i+[FFRCK]-[E_t]]^2+4K_i[E_t]]^{1/2}-(K_i+[FFRCK]-E_t)\}$$

in which $v_0$ is the initial rate of hydrolysis of the S2765 in the absence or inhibitor, and $K_i$ is an apparent inhibition constant for the enzyme-inhibitor complex.

Amidolytic Activity of the Activated Form of the Variant FpA-IVG

In order to compare the active site of the activated form of the variant FpA-IVG with that of normal FXa, the constants $k_{cat}$ and $K_M$ for the hydrolysis of two chromogenic substrates were determined: S2765 and benzyl-CO-Ile-Glu-(γ-OR)-Gly-Arg-pNA (SEQ ID NO:31) (S2222), marketed by BIOGENIC. The hydrolyses are carried out in kinetics buffer, at ambient temperature. Varying concentrations of substrate, of between 6 and 800 µM, are incubated with a fixed amount of the activated FX derivative (10 nM). The variation in absorbance at 405 nm as a function of time is recorded using an MR5000 microplate reader, and the initial rate of hydrolysis is estimated by linear regression of the absorbances corresponding at most to 10% hydrolysis. The constants $k_{cat}$ and $K_M$ are then estimated by non-linear regression of the variation of this initial rate as a function of the concentration of substrate, using the Michaelis-Menten equation.

The results obtained are summarized in Table VIII.

TABLE VIII

| | $k_{cat}\ s^{-1}$ | $K_M\ \mu M$ | $k_{cat}/K_M(\mu M^{-1}\cdot s^{-1})$ |
|---|---|---|---|
| | | S2222 | |
| FXa | 79 | 260 | 0.3 |
| Fpa-IVG | 56 | 194 | 0.3 |

TABLE VIII-continued

|  | $k_{cat} s^{-1}$ | $K_M \mu M$ | $k_{cat}/K_M (\mu M^{-1} \cdot s^{-1})$ |
|---|---|---|---|
|  | S2765 | | |
| FXa | 182 | 90 | 2.0 |
| Fpa-IVG | 125 | 49 | 2.5 |

The values of the $k_{cat}$ and the $K_M$, and also the ratio thereof, for S2222 and S2765 are similar even though they are not identical. This result suggests that the FXa which is generated by thrombin activation of the derivative FpA-IVG is indeed the same as that generated by RVV-X activation of FX.

Antithrombin Inhibition of the Activated Forms of FX Variants

Antithrombin is the main physiological inhibitor of FXa. It was therefore essential to determine the ability of antithrombin to interact with the activated forms of the FX derivatives, since any alteration of the plasma half-life would modify the procoagulant action of the FX derivative.

The inventors compared the ability of FXa to form a stable covalent complex with antithrombin, with that of the activated forms of the FX derivatives FpA-IVG and FpA-AVG. Demonstration of these complexes between the activated form of the FX derivatives (1 µM) and antithrombin (2 µM; purified from human plasma according to the technique described by MCKAY (Thromb. Res., 21, 375-25 382, 1981)) is carried out in the presence of 2 units/ml of heparin (KORDIA). The incubation is sustained for one hour at ambient temperature, and the reaction mixture is analysed by polyacrylamide gel electrophoresis (10%, crosslinking 29/1), after denaturation and reduction of the sample. The presence of covalent complexes between the activated FX derivative and antithrombin results in a decrease in the intensity of the band corresponding to antithrombin (60 kDa), a decrease in the intensity of the band corresponding to the activated form of the FX derivative (31 kDa), and the appearance of a new band, with a higher molecular weight (approximately 100 kDa), corresponding to the covalent complex.

Figure 5:
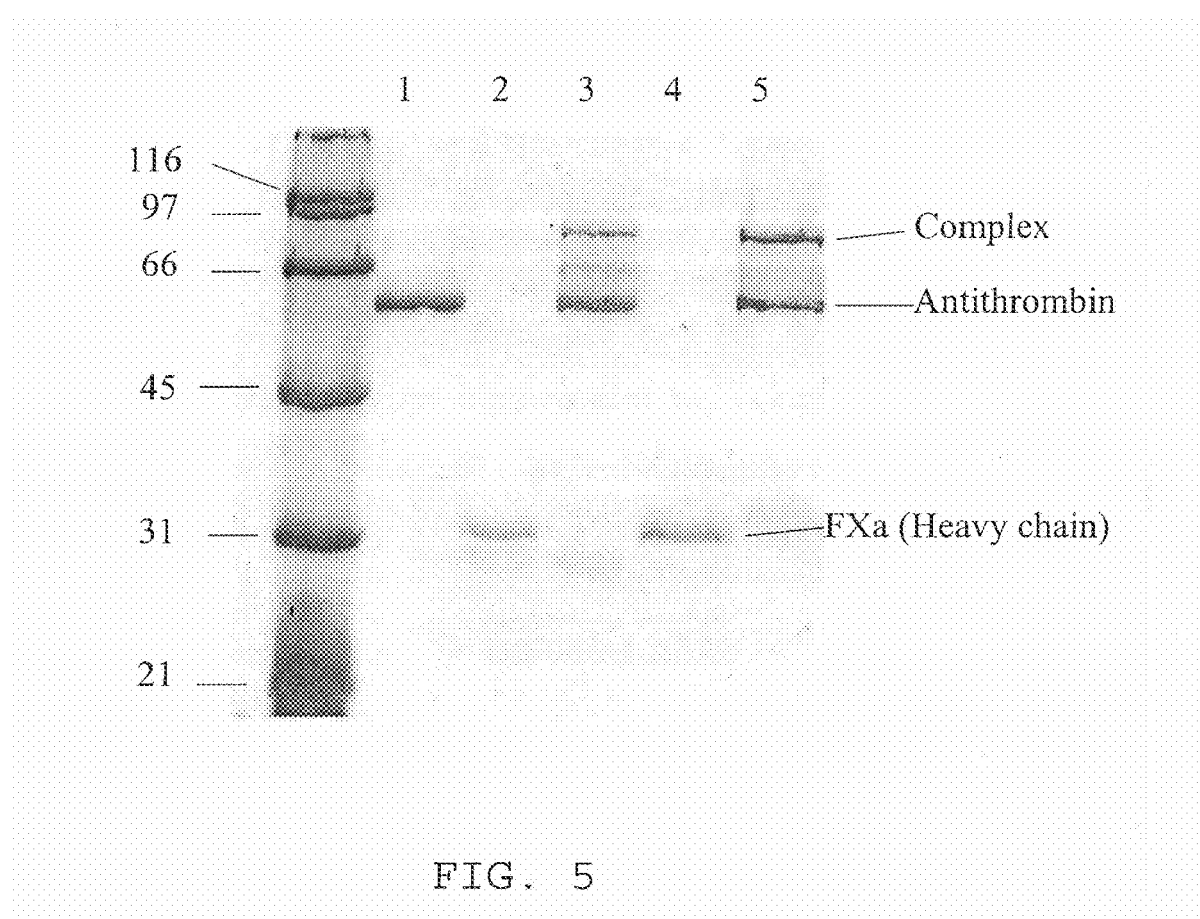
FIG. 5 A complex formation between the activated form of the FX derivative and antithrombin. Lane 1: antithrombin alone; lanes 2 and 3: (normal) FXa derivative without and with antithrombin; lanes 4 and 5: activated FpA-IVG derivative without and with antithrombin. The formation of a complex results in the appearance of a band of high molecular weight (lanes 3, 5), which is absent when the antithrombin is used alone or one of the activated forms of the FX derivatives (lanes 2, 4) is used alone. After electrophoresis, the proteins are stained with Coomassie blue.

The results are given in FIG. 5.

Lane 1: antithrombin alone; lanes 2 and 3: (normal) FXa derivative without and with antithrombin; lanes 4 and 5: activated FpA-IVG derivative without and with antithrombin. The formation of a complex results in the appearance of a band of high molecular weight (lanes 3, 5), which is absent when the antithrombin is used alone or one of the activated forms of the FX derivatives (lanes 2, 4) is used alone. After electrophoresis, the proteins are stained with Coomassie blue.

Determination of the Plasma Half-Life of the Activated Form of the FX Variant FpA-IVG The half-life of the activated form of the variant Fpa-IVG was compared to that of normal FXa.

To estimate this half-life, the residual activity of the variant is measured after incubation for varying times in normal plasma made unclottable by adding hirudin. The reaction mixture is made up of 80% (v/v) of a pool of citrated normal plasmas and of 20% of 50 mM Tris buffer, pH 7.5, containing 150 MM of NaCl, 40 mM CaCl$_2$, 0.5 mg/ml of bovine serum albumin, 400 U/ml of hirudin and 50 nM of FXa (normal or prepared from the variant FpA-IVG). After incubation, an aliquot of the plasma/FXa/hirudin mixture (40 µl) is added to 160 µl of 100 µM S2765, and the initial rate of hydrolysis of the substrate is measured by recording the increase in absorbance at 405 nm on an MR5000 microplate reader.

The half-life of each variant is estimated by non-linear regression of the variation in residual activity as a function of time, using an equation representing a first-order exponential decrease: $A_{(t)} = A_0 \exp^{(-k \cdot t)} + Cte$; in which $A_{(t)}$ represents the residual activity of the FXa at time t, $A_0$ represents its initial activity and k represents the first-order rate constant. The constant Cte is added to take into account a possible activity independent of that of the FXa (background noise). The plasma half-life is then calculated by dividing ln(2) by k.

The half-life values obtained (in seconds) are summarized in Table IX.

TABLE IX

|  | Half-life (seconds) |
|---|---|
| FXa (normal) | 77 |
| Fpa-IVG (activated) | 44 |

The plasma half-life of the activated form of the variant Fpa-IVG is therefore comparable to that of normal FXa, which suggests once again that these two molecules are similar, or even identical.

Anti-Haemophilic Activity of the FX Derivative FpA-IVG

The anti-haemophilic activity of the FX derivative FpA-IVG was tested by measuring the amount of thrombin produced over time: a test commonly called "thrombin generation time". This measurement is made in reconstituted normal plasma (DIAGNOSTICA STAGO, Asnières, France) or in FVIII-depleted plasma (also DIAGNOSTICA STAGO) to simulate severe haemophilia A. The clotting cascade is triggered by recalcification and addition of tissue factor. In order to be able to remove an aliquot at varying times, formation of the fibrin clot is inhibited by adding 2.5 mM of peptide Gly-Pro-Arg-Pro (GPRP; SIGMA ALDRICH) as described in LAUDANO et al. (Biochemistry 19, 1013-1019, 1980). The amount of thrombin present at a given moment after triggering of the clotting cascade is measured using a chromogenic substrate (S223S).

In practice, 150 µl of reconstituted plasma are mixed with 150 µl of kinetics buffer containing 2.5 mM of GPRP peptide and, optionally, 50 nM of FX derivative FpA-IVG or 1 U/ml of recombinant factor VIII (HEMOFILM, BAXTER. Maurepas, France, corresponding to the conventional treatment for haemophilia). This mixture is preincubated for 3 min at 37° C. The clotting cascade is then triggered by adding 300 µl of a solution of Neoplastine (DIAGNOSTICA STAGO) diluted to 1/100 in kinetics buffer. Aliquots of 20 µl are taken at varying times and immediately diluted to 1/5 in a stop solution (kinetics buffer containing 100 mM of benzamidine and 10 mM of EDTA). The amount of thrombin is estimated by adding 20 µl of each diluted aliquot to 180 µl of 200 µM S2238. The variation in absorbance at 405 nm as a function of time is recorded using an MR5000 microplate reader and the corresponding amount of thrombin is deduced with reference to a standard curve. The thrombin concentration increases rapidly during the first two minutes after addition of tissue factor, reaches a maximum, and then decreases slowly subsequent to its irreversible inhibition by antithrombin. The maximum reached, the time required to reach this maximum and the area under the curve are representative of the "thrombin generation time".

Figure 6:
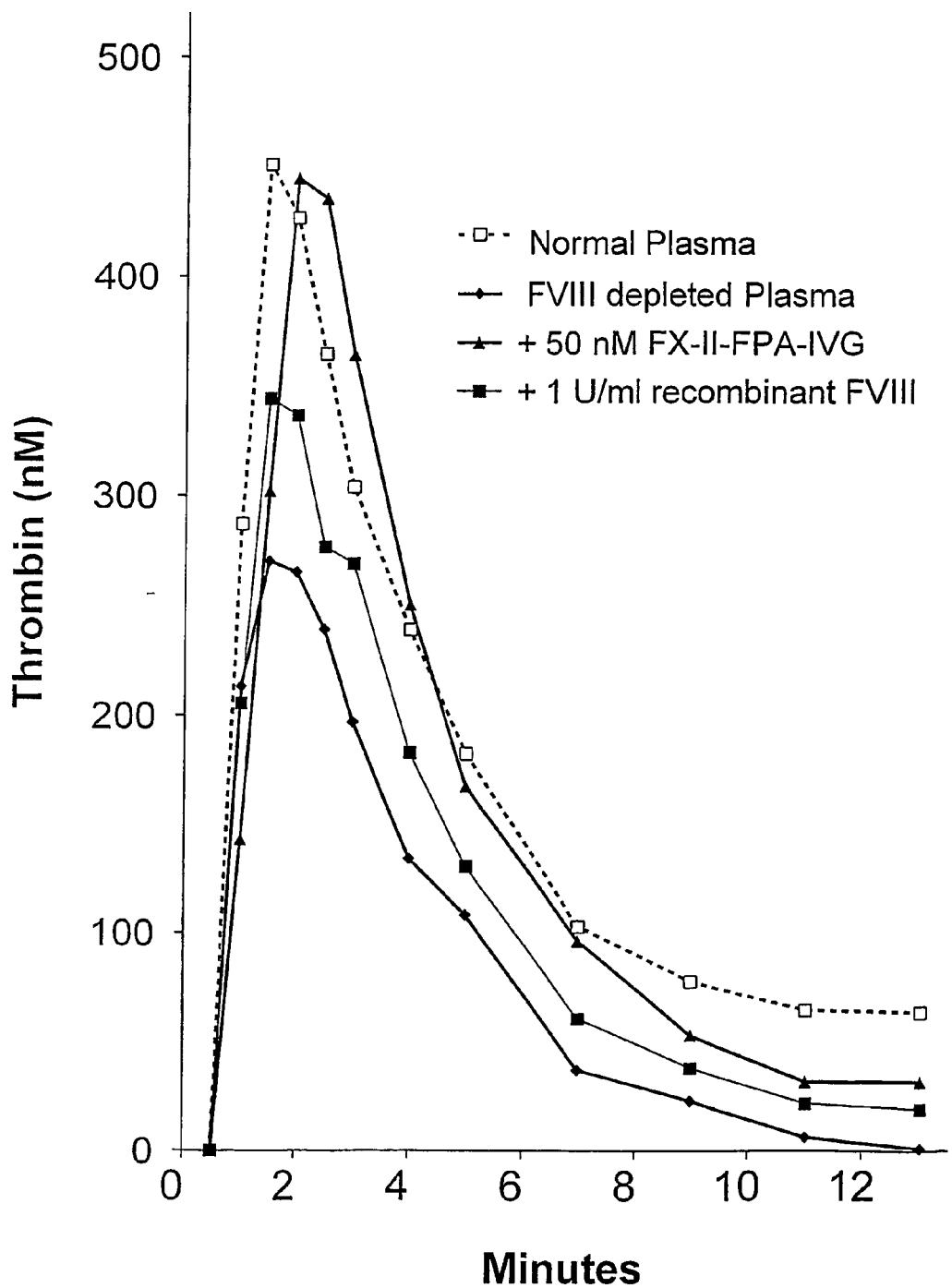
FIG. 6 The "thrombin generation times" obtained with reconstituted normal plasma, factor VIII-depleted plasma, factor VIII-depleted plasma supplemented with factor VIII at 1 U/ml and factor VIII-depleted plasma supplemented with 50 nM of the FX derivative FpA-IVG are given in FIG. 6.

The "thrombin generation times" obtained with reconstituted normal plasma, factor VIII-depleted plasma, factor VIII-depleted plasma supplemented with factor VIII at 1 U/ml and factor VIII-depleted plasma supplemented with 50 nM of the FX derivative FpA-IVG are given in FIG. 6.

The addition of 50 nM of FX derivative FpA-IVG makes it possible to restore a thrombin generation curve similar to that observed with a normal plasma, whereas the addition of 1 U/ml of factor VIII (the usual therapeutic dose) only partly restores this "thrombin generation".

CONCLUSION

Effects of Modifying the Activation Peptide of FX

When, in FX, the entire activation peptide (52 residues) is replaced with human FpA (from $P_{10}$ to $P_1$, i.e. the sequence DFLAEGGGVR-SEQ ID NO:2), the derivative becomes thrombin-activatable, unlike its normal homologue, this being under physiological conditions.

When this derivative is activated by thrombin, the product obtained is very similar, or even identical, to normal FXa (its covalent amino acid structure is identical). The catalytic activity, the plasma half-life, and its inhibition by antithrombin, are comparable. Overall, modification of the activation peptide of FX made it possible to obtain a thrombin-activatable derivative capable of correcting the thrombin generation time in a factor VIII-depleted plasma.

We claim:

1. A chimeric thrombin-cleavable derivative of a serine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a native cleavage site for thrombin of the protein C, wherein the amino acids $P_1'$-$P_2'$-$P_3'$ are represented by Leu-Ile-Asp, or the factor X, wherein the amino acids $P_1'$-$P_2'$-$P_3'$ are represented by Ile-Val-Gly.

2. An isolated nucleic acid molecule encoding the chimeric protein according to claim 1.

3. A recombinant vector, comprising the nucleic acid molecule according to claim 2.

4. An isolated host cell genetically transformed with the nucleic acid molecule according to claim 2.

5. A gene delivery system, comprising the nucleic acid molecule according to claim 2.

6. A composition comprising the gene delivery system according to claim 5.

7. A pharmaceutical composition, comprising the chimeric thrombin-cleavable derivative of claim 1 and a pharmaceutically acceptable excipient.

8. The pharmaceutical composition of claim 7, which is a procoagulant medicinal product, wherein the chimeric thrombin-cleavable derivative is a chimeric factor X.

9. The pharmaceutical composition of claim 7, which is a procoagulant medicinal product, wherein the serine protease derivative is a factor X derivative.

10. A chimeric thrombin-cleavable derivative of a seine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C, wherein the amino acids $P_2'$-$P_3'$ are represented by Ile-Asp, or the factor X, wherein the amino acids $P_2'$-$P_3'$ are represented by Val-Gly, and wherein the amino acid at position $P_1'$ of the protein C and/or the factor X is an alanine or a seine.

11. A serine protease derivative which is a protein C derivative obtained by a thrombin cleavage of the chimeric protein C derivative according to claim 10.

12. A chimeric thrombin-cleavable derivative of a serine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C, wherein the amino acids $P_1'$ and $P_3'$ are represented by Leu and Asp, respectively, or the factor X, wherein the amino acids $P_1'$ and $P_3'$ are represented by Ile and Gly, respectively, and wherein the amino acid at position $P_2'$ of the protein C and/or the factor X is a phenylalanine.

13. A seine protease derivative which is a protein C derivative obtained by a thrombin cleavage of the chimeric protein C derivative according to claim 12.

14. A serine protease derivative which is a factor X derivative obtained by a thrombin cleavage of the chimeric factor X derivative according to claim 12.

15. A chimeric thrombin-cleavable derivative of a seine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C, wherein the amino acids $P_1'$-$P_2'$ are represented by Leu-Ile, or the factor X, wherein the amino acids $P_1'$-$P_2'$ are represented by Ile-Val, and wherein the amino acid at position $P_3'$ of the protein C and/or the factor X is a glycine.

16. A chimeric thrombin cleavable derivative of serine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C, wherein the amino acids $P_3'$ is Asp, or the factor X, wherein the amino acids $P_3'$ is Gly, and wherein the amino acid at position $P_1'$ of the protein C and/or the factor X is an alanine or a seine, and the amino acid at position $P_2'$ of the protein C and/or the factor X is a phenylalanine.

17. A seine protease derivative which is a protein C derivative obtained by a thrombin cleavage of the chimeric protein C derivative according to claim 16.

18. A seine protease derivative which is a factor X derivative obtained by a thrombin cleavage of the chimeric factor X derivative according to claim 16.

19. A chimeric thrombin cleavable derivative of seine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C, wherein the amino acids $P_2'$ is Ile, or the factor X, wherein the amino acids $P_2'$ is Val, and wherein the amino acid at position $P_1'$ of the protein C and/or the factor X is an alanine or a serine, and the amino acid at position $P_3'$ of the protein C and/or the factor X is a glycine.

20. A seine protease derivative which is a protein C derivative obtained by a thrombin cleavage of the chimeric protein C derivative according to claim 19.

21. A chimeric thrombin cleavable derivative of serine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C, wherein the amino acids $P_1'$ is Leu, or the factor X, wherein the amino acids $P_1'$ is Ile, and wherein the amino acid at position $P_2'$ of the protein C and/or the factor X is phenylalanine, and the amino acid at position $P_3'$ of the protein C and/or the factor X is a glycine.

22. A seine protease derivative which is a protein C derivative obtained by a thrombin cleavage of a protein the chimeric C derivative according to claim 21.

23. A chimeric thrombin cleavable derivative of seine protease zymogen selected from the group consisting of protein C and factor X, wherein the native activation peptide of said zymogen is replaced with fibrinopeptide A, or a portion thereof, said replacement generates a thrombin-cleavable sequence $P_{10}P_9P_8P_7P_6P_5P_4P_3P_2P_1P_1'P_2'P_3'$ (SEQ ID NO:32), comprising amino acids $P_{10}$ to $P_1$ of fibrinopeptide A (SEQ ID NO:2) and amino acids $P_1'$-$P_2'$-$P_3'$ of a modified native cleavage site for thrombin of the protein C or the factor X, wherein the amino acid at position $P_1'$ is an alanine or a serine, the amino acid at position $P_2'$ is a phenylalanine and the amino acid at position $P_3'$ is a glycine.

24. A serine protease derivative which is a protein C derivative obtained by a thrombin cleavage of a the chimeric protein C derivative according to claim 23.

* * * * *

UNITED STATES PATENT AND TRADEMARK OFFICE
CERTIFICATE OF CORRECTION

PATENT NO. : 7,589,178 B2  Page 1 of 1
APPLICATION NO. : 10/492191
DATED : September 15, 2009
INVENTOR(S) : Le Bonniec et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1164 days.

Signed and Sealed this

Twenty-first Day of September, 2010

David J. Kappos
*Director of the United States Patent and Trademark Office*